US011918558B2

(12) United States Patent
Mehrling et al.

(10) Patent No.: US 11,918,558 B2
(45) Date of Patent: *Mar. 5, 2024

(54) TINOSTAMUSTINE FOR USE IN THE TREATMENT OF T-CELL PROLYMPHOCYTIC LEUKAEMIA

(71) Applicant: Purdue Pharma L.P., Stamford, CT (US)

(72) Inventors: Thomas Jorg Mehrling, Riehen (CH); Marco Herling, Cologne (DE)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,276

(22) Filed: Apr. 27, 2022

(65) Prior Publication Data

US 2022/0401417 A1 Dec. 22, 2022

Related U.S. Application Data

(63) Continuation of application No. 16/621,898, filed as application No. PCT/EP2018/065664 on Jun. 13, 2018, now Pat. No. 11,318,117.

(30) Foreign Application Priority Data

Jun. 13, 2017 (GB) ..................... 1709402

(51) Int. Cl.
*A61K 31/4184* (2006.01)
*A61K 9/00* (2006.01)
*A61P 35/02* (2006.01)

(52) U.S. Cl.
CPC ........ *A61K 31/4184* (2013.01); *A61K 9/0019* (2013.01); *A61P 35/02* (2018.01)

(58) Field of Classification Search
CPC ............................ A61K 31/4184; A61P 35/02
See application file for complete search history.

(56) References Cited

U.S. PATENT DOCUMENTS

| | | | |
|---|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,461,350 B2 | 6/2013 | Brittain et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 9,889,147 B2 | 2/2018 | Utku |
| 9,993,482 B2 | 6/2018 | Mehrling |
| 10,118,901 B2 | 11/2018 | Chen et al. |
| 10,406,138 B2 | 9/2019 | Mehrling et al. |
| 10,744,120 B2 | 8/2020 | Mehrling et al. |
| 11,266,631 B2 | 3/2022 | Mehrling et al. |
| 11,318,117 B2 | 5/2022 | Mehrling et al. |
| 11,413,276 B2 | 8/2022 | Mehrling |
| 11,419,853 B2 | 8/2022 | Mehrling et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2012/0289570 A1 | 11/2012 | Lengyel et al. |
| 2013/0030237 A1 | 1/2013 | Theuer |
| 2013/0209558 A1 | 8/2013 | Patzak et al. |
| 2014/0303218 A1 | 10/2014 | Chen et al. |
| 2015/0086551 A1 | 3/2015 | Chen et al. |
| 2015/0231198 A1 | 8/2015 | Carniti et al. |
| 2017/0095482 A1 | 4/2017 | Mehrling |
| 2017/0151218 A1 | 6/2017 | Mehrling et al. |
| 2018/0098969 A1 | 4/2018 | Mehrling et al. |
| 2019/0343807 A1 | 11/2019 | Mehrling et al. |
| 2020/0113870 A1 | 4/2020 | Mehrling |
| 2020/0261423 A1 | 8/2020 | Mehrling |
| 2021/0059989 A1 | 3/2021 | Mehrling et al. |
| 2021/0346351 A1 | 11/2021 | Mehrling et al. |
| 2022/0016084 A1 | 1/2022 | Hilgier et al. |
| 2022/0016085 A1 | 1/2022 | Hilgier et al. |
| 2022/0280485 A1 | 9/2022 | Mehrling et al. |
| 2023/0049350 A1 | 2/2023 | Mehrling et al. |
| 2023/0080216 A1 | 3/2023 | Mehrling |

FOREIGN PATENT DOCUMENTS

| | | |
|---|---|---|
| CL | 0501-2003 | 3/2003 |
| CL | 2272-2005 | 9/2005 |
| CL | 3232-2006 | 11/2006 |
| CN | 1764648 A | 4/2006 |
| CN | 101084876 A | 12/2007 |
| CN | 101928234 A | 12/2010 |
| CN | 102993102 A | 3/2013 |
| DE | 34727 A1 | 12/1964 |
| EP | 0717638 B1 | 3/2002 |
| EP | 3148529 A1 | 4/2017 |
| JP | 2007-531793 A | 11/2007 |
| KR | 10-2001-0031896 A | 4/2001 |

(Continued)

OTHER PUBLICATIONS

Advanced Accelerator Applications, Ongoing Clinical Studies with Advanced Accelerator Applications Pipeline Candidates. Retrieved online at: http://www.adacap.com/research-development/clinical-trials/. 6 pages, (2014).

(Continued)

*Primary Examiner* — Kamal A Saeed
(74) *Attorney, Agent, or Firm* — McCarter & English, LLP; Yu Lu

(57) ABSTRACT

T-PLL Therapy There is provided tinostamustine or a pharmaceutically acceptable salt thereof for use in the treatment of T-cell prolymphocytic leukemia (T-PLL) in a patient in need thereof.

9 Claims, 6 Drawing Sheets

(56) References Cited

FOREIGN PATENT DOCUMENTS

| | | |
|---|---|---|
| WO | WO-1995/030442 A1 | 11/1995 |
| WO | WO-2002/010161 A1 | 2/2002 |
| WO | WO-2002/22577 A2 | 3/2002 |
| WO | WO-2002/026696 A1 | 4/2002 |
| WO | WO-2002/055017 A2 | 7/2002 |
| WO | WO-2004/076386 A2 | 9/2004 |
| WO | WO-2005/013958 A1 | 2/2005 |
| WO | WO-2005/097747 A1 | 10/2005 |
| WO | WO-2006/120456 A1 | 11/2006 |
| WO | WO-2007/134169 A2 | 11/2007 |
| WO | WO-2008/050125 A1 | 5/2008 |
| WO | WO-2008/067027 A2 | 6/2008 |
| WO | WO-2009/036016 A1 | 3/2009 |
| WO | WO-2009/067453 A1 | 5/2009 |
| WO | WO-2009/100045 A1 | 8/2009 |
| WO | WO-2010/042568 A1 | 4/2010 |
| WO | WO-2010/075542 A1 | 7/2010 |
| WO | WO-2010/085377 A2 | 7/2010 |
| WO | WO-2010/097700 A1 | 9/2010 |
| WO | WO-2011/017448 A1 | 2/2011 |
| WO | WO-2013/039488 A1 | 3/2013 |
| WO | WO-2013/040286 A2 | 3/2013 |
| WO | WO-2013/113838 A1 | 8/2013 |
| WO | WO-2015/085289 A1 | 6/2015 |
| WO | WO-2015/180865 A1 | 12/2015 |
| WO | WO-2015/181154 A1 | 12/2015 |
| WO | WO-2015/181156 A1 | 12/2015 |
| WO | WO-2015/181157 A1 | 12/2015 |
| WO | WO-2016/087950 A1 | 6/2016 |
| WO | WO-2017/067474 A1 | 4/2017 |
| WO | 2018/229133 A1 | 12/2018 |

OTHER PUBLICATIONS

Aguado Bueno et al., Preliminary Experience of the Spanish Compassionate Use Registry of Bendamustine in Patients with Relapsed and/or Refractory Multiple Myeloma. Blood. 2012;120(21), Abstract 4035.

Al-Ani et al., Changes in urinary metabolomic profile during relapsing renal vasculitis. Sci Rep. Dec. 1, 2016;6:38074. 11 pages.

Alfarouk et al., Resistance to cancer chemotherapy: failure in drug response from ADME to P-gp. Cancer Cell Int. Jul. 15, 2015;15:71.

American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).

Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.

Andersson et al., Discovery of novel drug sensitivities in T-PLL by high-throughput ex vivo drug testing and mutation profiling. Leukemia. Aug. 14, 2017. pp. 1-14.

Andersson et al., Primary T-Prolymphocytic Leukemia (T-PLL) Cells are Sensitive to BCL-2 and HDAC Inhibitors: Results From High-Throughput Ex Vivo Drug Testing. Blood. 2013;122:3828. 6 pages.

Angelucci et al., Suberoylanilide hydroxamic acid partly reverses resistance to paclitaxel in human ovarian cancer cell lines. Gynecol Oncol. Dec. 2010;119(3):557-63.

Arun et al., The PARP inhibitor AZD2281 (Olaparib) induces autophagy/mitophagy in BRCA1 and BRCA2 mutant breast cancer cells. Int J Oncol. Jul. 2015;47(1):262-8.

Attal et al., Lenalidomide, Bortezomib, and Dexamethasone with Transplantation for Myeloma. The New England Journal of Medicine. Apr. 6, 2017;376:1311-1320.

Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.

Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22.

Bagchi, Bendamustine for advanced sarcoma. Lancet Oncol. Aug. 2007;8(8):674.

Baker et al., Investigation of bendamustine HCL in a phase 2 study in women with resistant ovarian cancer. Invest New Drugs. Feb. 2013;31(1):160-6.

Balfour et al., Bendamustine. Drugs. 2001;61(5):631-8.

Barendsen et al., Inhibition of TPA-induced monocytic differentiation in THP-1 human monocytic leukemic cells by staurosporine, a potent protein kinase C inhibitor. Leuk Res. 1990;14(5):467-74.

Bender, Across the divide. The blood-brain barrier represents a formidable obstacle for cancer drugs. Nature. Sep. 27, 2018;561:S46-S47.

Berenson et al., Phase I/II trial assessing bendamustine plus bortezomib combination therapy for the treatment of patients with relapsed or refractory multiple myeloma. Br J Haematol. Feb. 2013;160(3):321-30.

Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.

Besse et al., The first in class, alkylator-histone-deacetylase-inhibitor fusion molecule EDO-S101 in combination with proteasome inhibitors induces highly synergistic pro-apoptotic signaling through UPR activation and suppression of c-Myc and BCL2 in multiple meyloma. ASH, 2016.

Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.

Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.

Biete et al., Whole abdominal radiotherapy in ovarian cancer. Rep Pract Oncol Radiother. Mar. 23, 2010;15(2):27-30.

Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.

Bose et al., Histone deacetylase inhibitor (HDACI) mechanisms of action: emerging insights. Pharmacol Ther. Sep. 2014;143(3):323-36.

Botrugno et al., Molecular pathways: old drugs define new pathways: non-histone acetylation at the crossroads of the DNA damage response and autophagy. Clin Cancer Res. May 1, 2012;18(9):2436-42.

Braga et al., Crystal Polymorphism and Multiple Crystal Forms. Struct Bond. 2009;132:25-50.

Brewster et al., Cyclodextrins as pharmaceutical solubilizers. Adv Drug Deliv Rev. Jul. 30, 2007;59(7):645-66.

Bruce et al., Glioblastoma Multiforme Treatment & Management. Medscape. Retrieved online at: https://emedicine.medscape.com/article/283252-treatment. 20 pages. Jun. 14, 2017.

Buglio et al., Histone deacetylase inhibitors in Hodgkin lymphoma. Invest New Drugs. Dec. 2010;28 Suppl 1:S21-7.

Buglio et al., Vorinostat inhibits STAT6-mediated TH2 cytokine and TARC production and induces cell death in Hodgkin lymphoma cell lines. Blood. Aug. 15, 2008;112(4):1424-33.

Cai et al., Combination of bendamustine and entinostat synergistically inhibits proliferation of multiple myeloma cells via induction of apoptosis and DNA damage response. Cancer Lett. Jul. 28, 2013;335(2):343-50.

Cai et al., Discovery of 7-(4-(3-ethynylphenylamino)-7-methoxyquinazolin-6-yloxy)-N-hydroxyheptanamide (CUDc-101) as a potent multi-acting HDAC, EGFR, and HER2 inhibitor for the treatment of cancer. J Med Chem. Mar. 11, 2010;53(5):2000-9.

Cai et al., Solubilization of vorinostat by cyclodextrins. J Clin Pharm Ther. Oct. 2010;35(5):521-6.

(56) References Cited

OTHER PUBLICATIONS

Campos et al., Expression of nuclear receptor corepressors and class I histone deacetylases in astrocytic gliomas. Cancer Sci. Feb. 2011;102(2):387-92.

Chamberlain et al., Salvage therapy with bendamustine for methotrexate refractory recurrent primary CNS lymphoma: a retrospective case series. J Neurooncol. May 2014;118(1):155-62.

Chamberlain et al., Salvage therapy with single agent bendamustine for recurrent glioblastoma. J Neurooncol. Dec. 2011;105(3):523-30.

Chavez et al., Triple negative breast cancer cell lines: one tool in the search for better treatment of triple negative breast cancer. Breast Dis. 2010;32(1-2):35-48.

Chen et al., A 71-gene signature of TRAIL sensitivity in cancer cells. Mol Cancer Ther. Jan. 2012;11(1):34-44.

Chen et al., Dexamethasone and vorinostat cooperatively promote differentiation and apoptosis in Kasumi-1 leukemia cells through ubiquitination and degradation of AML1-ETO. Zhonghua Xue Ye Xue Za Zhi. Sep. 2013;34(9):741-4.

Chen et al., Discovery of a Novel, Efficient, and Scalable Route to Bendamustine Hydrochloride: The API in Treanda. Org Process Res Dev. 2011;15(5):1063-1072.

Chesi et al., Drug response in a genetically engineered mouse model of multiple myeloma is predictive of clinical efficacy. Blood. Jul. 12, 2012;120(2):376-85.

Chesi et al., Identification of Novel Therapeutic Targets in the Clinically Predictive Vk*MYC Mouse Model of Multple Myeloma. ASH, 2 pages. 2014.

Chesi et al., Identification of Novel Therapeutic Targets in the Clinically Predictive Vk*MYC Mouse Model of Multple Myeloma. Blood. 2014;124:415.

Chisholm et al., Emergence of drug tolerance in cancer cell populations: an evolutionary outcome of selection, nongenetic instability, and stress-induced adaptation. Cancer Res. Mar. 15, 2015;75(6):930-9.

Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.

Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.

Chow et al., In vitro induction of apoptosis of neoplastic cells in low-grade non-Hodgkin's lymphomas using combinations of established cytotoxic drugs with bendamustine. Haematologica. May 2001;86(5):485-93.

Ciavatta et al., Epigenetic basis for aberrant upregulation of autoantigen genes in humans with ANCA vasculitis. J Clin Invest. Sep. 2010;120(9):3209-19.

Ciusani et al., Valproic acid increases the in vitro effects of nitrosureas on human glioma cell lines. Oncol Res. 2007;16(10):453-63.

ClinicalTrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.

ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.

ClinicalTrials.gov, Phase 1 Trial of Dasatinib and Bendamustine in Chronic Lymphocytic Leukemia. ClinicalTrials Identifier: NCT00872976, Apr. 22, 2009. 3 pages.

ClinicalTrials.gov, Study of EDO-S101, A First-in-Class Alkylating HDACi Fusion Molecule, in Relapsed/Refractory Hematologic Malignancies. ClinicalTrials.gov Identifier: NTC02576496, 4 pages, Oct. 2015.

ClinicalTrials.gov, Study of the Safety, Pharmacokinetics and Efficacy of EDO-S101, in Patients With Advanced Solid TumorsClinical Trials Identifier: NCT03345485, Dec. 24, 2020. 12 pages.

Connors, Hodgkin lymphoma: special challenges and solutions. Hematol Oncol. Jun. 2015;33 Suppl 1:21-4.

Cooke et al., Spontaneous onset and transplant models of the Vk*MYC mouse show immunological sequelae comparable to human multiple myeloma. J Transl Med. Sep. 6, 2016;14:259. 12 pages.

Corazzelli et al., Efficacy and safety of bendamustine for the treatment of patients with recurring Hodgkin lymphoma. Br J Haematol. Jan. 2013;160(2):207-15.

Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Blood. 2015;126(23):2479. 7 pages.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1 page.

De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [https://ash.confex.com/ash/2015/webprogram/Paper84797.html]. 2 pages.

De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. Blood. 2015;126:2481, 5 pages.

Deangelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.

Desouza et al., Has the survival of patients with glioblastoma changed over the years? Br J Cancer. Jan. 19, 2016;114(2):146-50.

Detich et al., Valproate induces replication-independent active DNA demethylation. J Biol Chem. Jul. 25, 2003;278(30):27586-92.

Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.

Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.

Drogaris et al., Histone deacetylase inhibitors globally enhance h3/h4 tail acetylation without affecting h3 lysine 56 acetylation. Sci Rep. 2012;2:220. 12 pages.

Döhner et al., Diagnosis and management of acute myeloid leukemia in adults: recommendations from an international expert panel, on behalf of the European LeukemiaNet. Blood. Jan. 21, 2010;115(3):453-74.

Edoncology.com, The A-DAC Principle: A New Concept in Oncology Treatment. 3 pages, Sep. 2016.

EU Clinical Trials Register, EudraCT No. 2005-002051-41. 13 pages. Dec. 7, 2016.

EU Clinical Trials Register, EudraCT No. 2005-006083-57. 28 pages. Jun. 1, 2016.

Eurordis, Rare Diseases Europe, Why Research on Rare Diseases? Position Paper. Retrieved online at: www.eurordis.org. 14 pages. Oct. 2010.

(56) References Cited

OTHER PUBLICATIONS

Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.
Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.
Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.
Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.
Formenti et al., Results of a phase I-II study of adjuvant concurrent carboplatin and accelerated radiotherapy for triple negative breast cancer. Oncoimmunology. Dec. 27, 2016;6(3):e1274479, 8 pages.
Frew et al., Enhancing the apoptotic and therapeutic effects of HDAC inhibitors. Cancer Lett. Aug. 8, 2009;280(2):125-33.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Geurink et al., Incorporation of non-natural amino acids improves cell permeability and potency of specific inhibitors of proteasome trypsin-like sites. J Med Chem. Feb. 14, 2013;56(3):1262-75.
Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.
Gillis, HDAC Inhibition Appears to Sensitive Triple-Negative Breast Cancer Cells to Certain Treatments. Retrieved online at: https://www.onclive.com/conference-coverage/sabcs-2012/hdac-inhibition-appears-to-sensitize-triplenegative-breast-cancer-cells-to-certain-treatment, 2 pages, (2012).
Golub et al., Molecular classification of cancer: class discovery and class prediction by gene expression monitoring. Science. Oct. 15, 1999;286(5439):531-7.
Graham et al., T-cell prolymphocytic leukemia. Proc (Bayl Univ Med Cent). Jan. 2013;26(1):19-21.
Gravina et al., The novel CXCR4 antagonist, PRX177561, reduces tumor cell proliferation and accelerates cancer stem cell differentiation in glioblastoma preclinical models. Tumor Biology. Jun. 2017;1-17.
Greaves et al., Clonal evolution in cancer. Nature. Jan. 18, 2012;481(7381):306-13.
Griffith et al., A novel anti-cancer bifunctional platinum drug candidate with dual DNA binding and histone deacetylase inhibitory activity. Chem Commu (Camb). Nov. 28, 2009;(44):6735-7.
Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.
Groselj et al., Histone deacetylase inhibitors as radiosensitisers: effects on DNA damage signalling and repair. Br J Cancer. Mar. 5, 2013;108(4):748-54.
Guntner et al., Cerebrospinal fluid penetration of targeted therapeutics in pediatric brain tumor patients. Acta Neuropathol Commun. Jun. 3, 2020;8(1):78, 13 pages.
Hancock et al., HDAC inhibitor therapy in autoimmunity and transplantation. Ann Rheum Dis. Apr. 2012;71 Suppl 2:i46-54.
Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.
Hartmann et al., Bendamustine hydrochloride in patients with refractory soft tissue sarcoma: a noncomparative multicenter phase 2 study of the German sarcoma group (AIO-001). Cancer. Aug. 15, 2007;110(4):861-6.
Hedgethorne et al., FORETINIB, c-Met and VEGFR-2 Inhibitor Oncolytic. Drugs of the Future. 2010;35(11):893-902.
Hegi et al., MGMT gene silencing and benefit from temozolomide in glioblastoma. N Engl J Med. Mar. 10, 2005;352(10):997-1003.
Her et al., Targeting DNA Double-strand Break Repair in Cancer Therapy. Journal of Molecular and Genetic Medicine. Dec. 31, 2015;9:e106, 1 page.
Herbaux et al., Bendamustine is effective in T-cell prolymphocytic leukaemia. Br J Haematol. Mar. 2015;168(6):916-9.
Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19). J Cancer Res Clin Oncol. Feb. 2006;132(2):105-12.
Herold et al., BOP versus COP in Advanced Low Grade Non-Hodgkin's Lymphomas—Results of a Randomized Multicenter Study. Blood. 1999;94:262b. Abstract 4382.
Hideshima et al., Mechanism of action of proteasome inhibitors and deacetylase inhibitors and the biological basis of synergy in multiple myeloma. Mol Cancer Ther. Nov. 2011;10(11):2034-42.
Hoffman, Brentuximab Vedotin Plus Bendamustine Active in Heavily Pretreated Hodgkin Lymphoma, ALCL. Cancer Therapy Advisor, Dec. 7, 2015. 2 pages. retreived online at: http://www.cancertherapyadvisor.com/ash-2015/hodgkin-lymphoma-alcl-brentuximab-vedotin-better-treatment-risk/article/458249/.
Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.
Howlader et al., Contributions of Subtypes of Non-Hodgkin Lymphoma to Mortality Trends. Cancer Epidemiol Biomarkers Prev. Jan. 2016;25(1):174-9.
Hummel et al., A pediatric phase 1 trial of vorinostat and temozolomide in relapsed or refractory primary brain or spinal cord tumors: a Children's Oncology Group phase 1 consortium study. Pediatr Blood Cancer. Sep. 2013;60(9):1452-7.
Ihle et al., HR23b expression is a potential predictive biomarker for HDAC inhibitor treatment in mesenchymal tumours and is associated with response to vorinostat. The Journal of Pathology: Clinical Research. 2016;2:59-71.
Jagannath et al., Bortezomib in combination with dexamethasone for the treatment of patients with relapsed and/or refractory multiple myeloma with less than optimal response to bortezomib alone. Haematologica. Jul. 2006;91(7):929-34.
Jawhari et al., In Vitro and In Vivo Preclinical Activity of EDO-S101 in Hodgkin Lymphoma. Haematologica. 2016;101(s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kalin et al., Creating zinc monkey wrenches in the treatment of epigenetic disorders. Curr Opin Chem Biol. Jun. 2009;13(3):263-71.
Kallenberg, Pathogenesis and treatment of ANCA-associated vasculitides. Clin Exp Rheumatol. Jul.-Aug. 2015;33(4 Suppl 92):S11-4.
Kallenberg, Pathogenesis of ANCA-associated vasculitides. Ann Rheum Dis. Mar. 2011;70 Suppl 1:i59-63.
Kalsi et al., The impact of low-grade toxicity in older people with cancer undergoing chemotherapy. Br J Cancer. Dec. 9, 2014;111(12):2224-8.

(56) References Cited

OTHER PUBLICATIONS

Kampa-Schittenhelm et al., Quizartinib (AC220) is a potent second generation class III tyrosine kinase inhibitor that displays a distinct inhibition profile against mutant-FLT3, -PDGFRA and -KIT isoforms. Molecular Cancer. 2013;12:19, 15 pages.
Kaufman et al., Lenalidomide. Bortezomib. and Dexamethasone (RVD) in Combination with Vorinostat as Front-Line Therapy for Patients with Multiple Myeloma (MM): Results of a Phase 1 Study. Blood. 2012;120, Abstract No. 336. 2 pages. ASH Annual Meeting.
Keating et al., Bendamustine. Nat Rev Drug Discov. Jun. 2008;7(6):473-4.
Khot et al., Panobinostat in lymphoid and myeloid malignancies. Expert Opin Investig Drugs. Sep. 2013;22(9):1211-23.
Kigawa, New strategy for overcoming resistance to chemotherapy of ovarian cancer. Yonago Acta Med. Jun. 2013;56(2):43-50.
Kim et al., Histone deacetylase inhibitors: molecular mechanisms of action and clinical trials as anti-cancer drugs. Am J Transl Res. Feb. 2011;3(2):166-79.
Knauf, Bendamustine in the treatment of chronic lymphocytic leukemia. Expert Rev Anticancer Ther. Feb. 2009;9(2):165-74.
Knittel et al., Two mouse models reveal an actionable PARP1 dependence in aggressive chronic lymphocytic leukemia. Nat Commun. Jul. 28, 2017;8(1):153. 13 pages.
Kollmannsberger et al., Phase II study of bendamustine in patients with relapsed or cisplatin-refractory germ cell cancer. Anticancer Drugs. Aug. 2000;11(7):535-9.
Koster et al., Carboplatin in Combination with Bendamustine in Previously Untreated Patients with Extensive-Stage Small Cell Lung Cancer (SCLC). Clin Drug Investig. 2004;24(10):611-8.
Kotzin et al., Reversal of nzb/nzw disease with total lymphoid irradiation. J Exp Med. Aug. 1, 1979;150(2):371-8.
Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.
Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.
Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.
Krause et al., Tyrosine kinases as targets for cancer therapy. N Engl J Med. Jul. 14, 2005;353(2):172-87.
Kumar et al., Histone deacetylase inhibitors induce cell death in supratentorial primitive neuroectodermal tumor cells. Oncol Rep. Nov. 2006; 16(5):1047-52.
Lala et al., Role of nitric oxide in tumor progression: lessons from experimental tumors. Cancer Metastasis Rev. Mar. 1998;17(1):91-106.
Layman et al., Severe and prolonged lymphopenia observed in patients treated with bendamustine and erlotinib for metastatic triple negative breast cancer. Cancer Chemother Pharmacol. May 2013;71(5):1183-90.
Le Moigne et al., The p97 Inhibitor CB-5083 is a Unique Disrupter of Protein Homeostasis in Models of Multiple Myeloma. Molecular Cancer Therapeutics. Nov. 2017;16(11):2375-2386.
Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.
Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.
Lentzsch et al., Combination of bendamustine, lenalidomide, and dexamethasone (BLD) in patients with relapsed or refractory multiple myeloma is feasible and highly effective: results of phase 1/2 open-label, dose escalation study. Blood. May 17, 2012;119(20):4608-13.
Leoni et al., Bendamustine (Treanda) displays a distinct pattern of cytotoxicity and unique mechanistic features compared with other alkylating agents. Clin Cancer Res. Jan. 1, 2008;14(1):309-17.
Leoni, Bendamustine: rescue of an effective antineoplastic agent from the mid-twentieth century. Semin Hematol. Apr. 2011;48 Suppl 1:S4-11.
Leung-Hagesteijn et al., Xbp1s-negative tumor B cells and pre-plasmablasts mediate therapeutic proteasome inhibitor resistance in multiple myeloma. Cancer Cell. Sep. 9, 2013;24(3):289-304.
Li et al., Pharmacokinetics of bendamustine in the central nervous system: chemoinformatic screening followed by validation in a murine model. MedChemComm. 2012;3:1526-1530.
Liby et al., Elevated and Deregulated Expression of HDAC3 in Human Astrocytic Glial Tumours. Folia Biologica (Praha). 2006;52:21-33.
Lin et al., Anti-rheumatic activities of histone deacetylase (HDAC) inhibitors in vivo in collagen-induced arthritis in rodents. Br J Pharmacol. Apr. 2007;150(7):862-72.
Lin et al., Treatment of Brain Metastases. J Clin Oncol. Oct. 20, 2015;33(30):3475-84.
Little et al., Experimental autoimmune vasculitis: an animal model of anti-neutrophil cytoplasmic autoantibody-associated systemic vasculitis. Am J Pathol. Apr. 2009;174(4):1212-20.
Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.
Liu et al., A DNA/HDAC dual-targeting drug CY190602 with significantly enhanced anticancer potency. EMBO Mol Med. 12 pages, Published online: Mar. 9, 2015.
Liu et al., Effects of suberoylanilide hydroxamic acid (SAHA) combined with paclitaxel (PTX) on paclitaxel-resistant ovarian cancer cells and insights into the underlying mechanisms. Cancer Cell Int. Nov. 26, 2014;14(1):112, 11 pages.
Liu, Characterization of TCL1-Tg:P53-/-Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.
Loftsson et al., Historical Perspectives: Cyclodextrins and their pharmaceutical applications. International Journal of Pharmaceutics. 2007;329:1-11.
Loibl et al., Multicenter Phase II Study with Weekly Bendamustine and Paclitaxel as First-or Later-Line Therapy in Patients with Metastatic Breast Cancer: RiTa II Trial. Breast Care (Basel). Dec. 2011;6(6):457-461.
Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.
Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.
Lopez-Iglesias et al., Preclinical anti-myeloma activity of the alkylating-HDACi Fusion Molecule EDO-S101 Through DNA-damaging and HDACi Effects. Haematologica. 2014;99(s1):354-355, Abstract P942.
Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.
Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.
Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.
Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.

(56) References Cited

OTHER PUBLICATIONS

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.

Ludwig et al., Bendamustine-bortezomib-dexamethasone is an active and well-tolerated regimen in patients with relapsed or refractory multiple myeloma. Blood. Feb. 13, 2014;123(7):985-91.

Marchion et al., Development of histone deacetylase inhibitors for cancer treatment. Expert Rev Anticancer Ther. Apr. 2007;7(4):583-98.

Marks, Discovery and development of SAHA as an anticancer agent. Oncogene. Feb. 26, 2007;26(9):1351-6.

Marmion et al., Hydroxamic Acids—An Intriguing Family of Enzyme Inhibitors and Biomedical Ligands. Eur J Inorg Chem. 2004(15):3003-3016.

McInnis et al., Dysregulation of autoantigen genes in ANCA-associated vasculitis involves alternative transcripts and new protein synthesis. J Am Soc Nephrol. Feb. 2015;26(2):390-9.

Meanwell, Synopsis of some recent tactical application of bioisosteres in drug design. J Med Chem. Apr. 28, 2011;54(8):2529-91.

Medline AN—NLM24103869, Chen et al., Dexamethasone and Vorinostat Cooperatively Promote Differentiation and Apoptosis in Kasumi-1 Leukemia Cells Through Ubiquitination and Degradation of AML1-ETO. 2 pages.

Medline/NLM AN: NLM24998648, 1 page.

Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.

Mehrling et al., Is there hope to treat glioblastoma effectively? CNS Oncol. 2015;4(6):377-9.

Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.

Mehrling, Chemotherapy is getting 'smarter'. Future Oncol. 2015;11(4):549-52.

Mehrling, First in human clinical trails to commence Q3 2015. Mundipharma EDO GmbH. Retrieved online at: http://mundipharma-edo.com. Jul. 31, 2015. 2 pages.

Mehrling, First-in-human clinical trial of its lead compound, EDO-S101. Mundipharma EDO GmbH. Retrieved online at: http://mundipharma-edo.com. May 3, 2016. 2 pages.

Mehrling, Fusion Therapy, a New Approach to Combining Treatments. Drug Discovery World. 2016;71-76.

Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-cancer-compound-edo-s101-for-the-treatment-of-patients-with-relapsedrefractory-haematologic-malignancies-and-s/. 2 pages, Jul. 31, 2015.

Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.

Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.

Miller et al., Histone deacetylase inhibitors. J Med Chem. Nov. 20, 2003;46(24):5097-116.

Min et al., Histone deacetylase inhibitor, suberoylanilide hydroxamic acid (SAHA), enhances anti-tumor effects of the poly (ADP-ribose) polymerase (PARP) inhibitor olaparib in triple-negative breast cancer cells. Breast Cancer Res. Mar. 7, 2015;17:33, 13 pages.

Minucci et al., Histone deacetylase inhibitors and the promise of epigenetic (and more) treatments for cancer. Nat Rev Cancer. Jan. 2006;6(1):38-51.

Mishra et al., Histone deacetylase inhibitors modulate renal disease in the MRL-Ipr/Ipr mouse. J Clin Invest. Feb. 2003;111(4):539-52.

Moosman et al., Weekly treatment with a combination of bortezomib and bendamustine in relapsed or refractory indolent non-Hodgkin lymphoma. Leuk Lymphoma. Jan. 2010;51(1):149-52.

Moradei et al., Histone deacetylase inhibitors: latest developments, trends and prospects. Curr Med Chem Anticancer Agents. Sep. 2005;5(5):529-60.

Moreau et al., Phase 1b Dose Escalation Study of Oral Quisinostat, a Histone Deacetylase Inhibitor (HDACi), In Combination With Velcade (Bortezomib) and Dexamethasone for Patients With Relapsed Multiple Myeloma (MM). Blood. Nov. 15, 2013;122(21):1932.

Moreau et al., Proteasome inhibitors in multiple myeloma: 10 years later. Blood. Aug. 2, 2012;120(5):947-59.

Moscovitch et al., Successful treatment of autoimmune manifestations in MRL/I and MRL/n mice using total lymphoid irradiation (TLI). Exp Mol Pathol. Feb. 1983;38(1):33-47.

Moskowitz et al., Phase II study of bendamustine in relapsed and refractory Hodgkin lymphoma. J Clin Oncol. Feb. 1, 2013;31(4):456-60.

Moskowitz, Bendamustine: a bridge to longer term solutions in heavily treated Hodgkin lymphoma. Leuk Lymphoma. Nov. 2013;54(11):2339-40.

MRF, Melanoma Research Foundation, Melanoma Central Nervous System Metastases, Current Approaches, Challenges and Opportunities. 5 pages (2015).

Munakata et al., The discovery and the development of bendamustine for the treatment of non-Hodgkin lymphoma. Expert Opin Drug Discov. Nov. 2016;11(11):1123-1130.

Munker et al., Activity of Tyrosine Kinase Inhibitors in Multiple Myeloma. Blood. 2007;110(11):274B, Abstract 4804.

National Institute of Health, Cancer. MedlinePlus. Retrieved online at: http://www.nlm.nih.gov/medlineplus/cancer.html. 10 pages. Apr. 16, 2007.

O'Donnell et al., Cancer pharmacoethnicity: ethnic differences in susceptibility to the effects of chemotherapy. Clin Cancer Res. Aug. 1, 2009;15(15):4806-14.

O'Reilly et al., Urinary Soluble CD163 in Active Renal Vasculitis. J Am Soc Nephrol. Sep. 2016;27(9):2906-16.

Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.

Ocio et al., In vitro and in vivo rationale for the triple combination of panobinostat (LBH589) and dexamethasone with either bortezomib or lenalidomide in multiple myeloma. Haematologica. May 2010;95(5):794-803.

Ocio et al., Phase I study of plitidepsin in combination with bortezomib and dexamethasone in patients with relapsed and/or refractory multiple myeloma. Journal of Clinical Oncology. 2016;34:Abstract 8006, 1 page.

Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110: Abstract 1514. ASH Annual Meeting.

Ocio, Epigenetic regulation and HAC inhibitors, Still a role for these agents in MM? Institute of Biomedical Research of Salamanca, University of Salamanca, Cancer Research Center, Slideshow. 32 pages, (2016).

Offidani et al., Efficacy and tolerability of bendamustine, bortezomib and dexamethasone in patients with relapsed-refractory multiple myeloma: a phase II study. Blood Cancer J. Nov. 22, 2013;3:e162.

Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.

(56) References Cited

OTHER PUBLICATIONS

Ol et al., Synergistic induction of NY-ESO-1 antigen expression by a novel histone deacetylase inhibitor, valproic acid, with 5-aza-2'-deoxycytidine in glioma cells. J Neurooncol. Mar. 2009;92(1):15-22.

Oken et al., Toxicity and response criteria of the Eastern Cooperative Oncology Group. Am J Clin Oncol. Dec. 1982;5(6):649-55.

Oriol et al., Outcome after relapse of acute lymphoblastic leukemia in adult patients included in four consecutive risk-adapted trials by the PETHEMA Study Group. Haematologica. Apr. 2010;95(4):589-596.

Paris et al., Histone deacetylase inhibitors: from bench to clinic. J Med Chem. Mar. 27, 2008;51(6):1505-29.

Phan et al., An update on ethnic differences in drug metabolism and toxicity from anti-cancer drugs. Expert Opin Drug Metab Toxicol. Nov. 2011;7(11):1395-410.

Phiel et al., Histone deacetylase is a direct target of valproic acid, a potent anticonvulsant, mood stabilizer, and teratogen. J Biol Chem. Sep. 28, 2001;276(39):36734-41.

Pitha et al., Parenteral hydroxypropyl cyclodextrins: intravenous and intracerebral administration of lipophiles. J Pharm Sci. Jun. 1994;83(6):833-7.

Poenisch et al., Bendamustine/Prednisone Versus Melphalane/Prednisone in the Primary Treatment of Multiple Myeloma: an Updated Analysis of the 94BP01 Protocol. Blood. 2000;96(Suppl 1:759a), Abstract 3284, Poster Board Session 748-111.

Puetzer et al., Towards novel strategies of targeting specific vulnerabilities of T-PLL cells. AACR Annual Meeting. Jul. 2017;77(Suppl 13), Abstract 1372.

Ponisch et al., Combined bendamustine, prednisone and bortezomib (BPV) in patients with relapsed or refractory multiple myeloma. J Cancer Res Clin Oncol. Mar. 2013;139(3):499-508.

Pönisch et al., Treatment of bendamustine and prednisone in patients with newly diagnosed multiple myeloma results in superior complete response rate, prolonged time to treatment failure and improved quality of life compared to treatment with melphalan and prednisone—a randomized phase III study of the East German Study Group of Hematology and Oncology (OSHO). J Cancer Res Clin Oncol. Apr. 2006;132(4):205-12.

Qian et al., Activity of PXD101, a histone deacetylase inhibitor, in preclinical ovarian cancer studies. Mol Cancer Ther. Aug. 2006;5(8):2086-95.

Rajewski et al., Preliminary safety evaluation of parenterally administered sulfoalkyl ether beta-cyclodextrin derivatives. J Pharm Sci. Aug. 1995;84(8):927-32.

Rang et al., Glucocorticoids. Rang and Dale's Pharmacology, Sixth Edition. Elsevier, Limited, 3 pages, (2007).

Rang et al., Rang and Dale's Pharmacology, Sixth Edition. Churchill Livingstone Elsevier. Chapter 51, p. 729, (2007).

Rasheed et al., Histone deacetylase inhibitors in cancer therapy. Expert Opin Investig Drugs. May 2007;16(5):659-78.

Rasschaert et al., A phase I study of bendamustine hydrochloride administered day 1+2 every 3 weeks in patients with solid tumours. Br J Cancer. Jun. 4, 2007;96(11):1692-8.

Rasschaert et al., A phase I study of bendamustine hydrochloride administered once every 3 weeks in patients with solid tumors. Anticancer Drugs. Jun. 2007;18(5):587-95.

Reagan-Shaw et al., Dose translation from animal to human studies revisited. FASEB J. Mar. 2008;22(3):659-61.

Regna et al., HDAC expression and activity is upregulated in diseased lupus-prone mice. Int Immunopharmacol. Dec. 2015;29(2):494-503.

Reilly et al., Modulation of renal disease in MRL/lpr mice by suberoylanilide hydroxamic acid. J Immunol. Sep. 15, 2004;173(6):4171-8.

Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.

Richardson et al., PANORAMA 2: panobinostat in combination with bortezomib and dexamethasone in patients with relapsed and bortezomib-refractory myeloma. Blood. Oct. 3, 2013;122(14):2331-7.

Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).

Ryu et al., Valproic acid downregulates the expression of MGMT and sensitizes temozolomide-resistant glioma cells. J Biomed Biotechnol. 2012;2012:987495. 9 pages.

Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.

Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.

Santacruz et al., The prognostic impact of minimal residual disease in patients with chronic lymphocytic leukemia requiring first-line therapy. Haematologica. May 2014;99(5):873-80.

Sarkaria et al., Mechanisms of chemoresistance to alkylating agents in malignant glioma. Clin Cancer Res. May 15, 2008;14(10):2900-8.

Saulnier et al., An Efficient Method for the Synthesis of Guanidino Prodrugs. Bioorganic & Medicinal Chemistry Letters. 1994;4(16):1985-1990.

Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.

Schoffski et al., Repeated administration of short infusions of bendamustine: a phase I study in patients with advanced progressive solid tumours. J Cancer Res Clin Oncol. Jan. 2000;126(1):41-7.

Schöffski et al., Weekly administration of bendamustine: a phase I study in patients with advanced progressive solid tumours. Ann Oncol. Jun. 2000;11(6):729-34.

Serra et al., Co-clinical trial of olaparib in breast and ovarian patient-derived tumor xenografts (PDX) enables the identification of response biomarkers. Clin Cancer Res. 2016;22(Suppl 16):Abstract B02, 4 pages.

Shah et al., Comprehensive analysis of MGMT promoter methylation: correlation with MGMT expression and clinical response in GBM. PLoS One. Jan. 7, 2011;6(1):e16146.

Shipley et al., Acute myelogenous leukemia. Exp Hematol. Jun. 2009;37(6):649-58.

Siegel et al., Vorinostat in combination with lenalidomide and dexamethasone in patients with relapsed or refractory multiple myeloma. Blood Cancer J. Feb. 21, 2014;4(2):e182, 6 pages.

Simon, Optimal two-stage designs for phase II clinical trials. Control Clin Trials. Mar. 1989;10(1):1-10.

Song et al., Increased expression of histone deacetylase 2 is found in human gastric cancer. APMIS. 2005;113:264-8.

Stiborová et al., The synergistic effects of DNA-targeted chemotherapeutics and histone deacetylase inhibitors as therapeutic strategies for cancer treatment. Curr Med Chem. 2012;19(25):4218-38.

Storer, Design and analysis of phase I clinical trials. Biometrics. Sep. 1989;45(3):925-37.

Sturn et al., Genesis: cluster analysis of microarray data. Bioinformatics. Jan. 2002;18(1):207-8.

Tago et al., Repeated 0.5-Gy gamma irradiation attenuates autoimmune disease in MRL-lpr/lpr mice with suppression of CD3+CD4-CD8-B220+ T-cell proliferation and with up-regulation of CD4+CD25+Foxp3+ regulatory T cells. Radiat Res. Jan. 2008;169(1):59-66.

Takai et al., Human ovarian carcinoma cells: histone deacetylase inhibitors exhibit antiproliferative activity and potently induce apoptosis. Cancer. Dec. 15, 2004;101(12):2760-70.

Tesar et al., Limitations of standard immunosuppressive treatment in ANCA-associated vasculitis and lupus nephritis. Nephron Clin Pract. 2014;128(3-4):205-15.

(56) References Cited

OTHER PUBLICATIONS

Thurn et al., Rational therapeutic combinations with histone deacetylase inhibitors for the treatment of cancer. Future Oncol. Feb. 2011;7(2):263-83.
Topalian et al., Immune checkpoint blockade: a common denominator approach to cancer therapy. Cancer Cell. Apr. 13, 2015;27(4):450-61.
Trivedi et al., Management of Chemotherapy-Induced Peripheral Neuropathy. American Journal of Hematology / Oncology. Jan. 2015;11(1):4-10.
Tsai et al., Valproic Acid Enhanced Temozolomide-Induced Anticancer Activity in Human Glioma Through the p53-PUMA Apoptosis Pathway. Front Oncol. Oct. 1, 2021;11:722754, 13 pages.
Tseng et al., A comparison of the molecular subtypes of triple-negative breast cancer among non-Asian and Taiwanese women. Breast Cancer Res Treat. Jun. 2017;163(2):241-254.
Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Van Krieken, New developments in the pathology of malignant lymphoma. A review of the literature published from Jan.-Apr. 2016. J Hematop. Jun. 13, 2016;9(2):73-83.
Viel et al., Optimizing glioblastoma temozolomide chemotherapy employing lentiviral-based anti-MGMT shRNA technology. Mol Ther. Mar. 2013;21(3):570-9.
Vippagunta et al., Crystalline Solids. Advanced Drug Delivery Reviews. 2001;48:3-26.
Vlachostergios et al., Bortezomib downregulates MGMT expression in T98G glioblastoma cells. Cell Mol Neurobiol. Apr. 2013;33(3):313-8.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Vyas et al., Cyclodextrin based novel drug delivery systems. J Incl Phenom Macrocycl Chem. 2008;62:23-42.
Wang et al., Effect of histone deacetylase inhibitor NL101 on rat neurons. Zhejiang Da Xue Bao Yi Xue Ban. May 2014;43(3):265-272. Abstract Only. 2 pages.
Wang et al., Independent validation of a model using cell line chemosensitivity to predict response to therapy. J Natl Cancer Inst. Sep. 4, 2013;105(17):1284-91.
Wang et al., Phase 1 trial of linifanib (ABT-869) in patients with refractory or relapsed acute myeloid leukemia. Leuk Lymphoma. Aug. 2012;53(8):1543-51.
Wang et al., Toward selective histone deacetylase inhibitor design: homology modeling, docking studies, and molecular dynamics simulations of human class I histone deacetylases. J Med Chem. Nov. 3, 2005;48(22):6936-47.
Watanabe et al., Modulation of renal disease in MRL/lpr mice genetically deficient in the alternative complement pathway factor B. J Immunol. Jan. 15, 2000;164(2):786-94.
Weil et al., Breast cancer metastasis to the central nervous system. Am J Pathol. Oct. 2005;167(4):913-20.
White, FDA accepts Mundipharma EDO's IND for EDO-S101. European Pharmaceutical Review. 4 pages, Aug. 3, 2015.
Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.
Wikipedia, Triple-negative breast cancer. Retrieved online at: https://en.wikipedia.org/wiki/Triple-negative_breast_cancer. 7 pages, Feb. 20, 2017.

Wilson et al., Histone deacetylase 3 (HDAC3) and other class I HDACs regulate colon cell maturation and p21 expression and are deregulated in human colon cancer. J Biol Chem. May 12, 2006;281(19):13548-58.
Wilson et al., Relationship of p53, bcl-2, and tumor proliferation to clinical drug resistance in non-Hodgkin's lymphomas. Blood. Jan. 15, 1997;89(2):601-9.
Witzel et al., Long-term tumor remission under trastuzumab treatment for HER2 positive metastatic breast cancer—results from the HER-OS patient registry. BMC Cancer. Nov. 4, 2014;14:806. 7 pages.
Xiao et al., Antineutrophil cytoplasmic autoantibodies specific for myeloperoxidase cause glomerulonephritis and vasculitis in mice. J Clin Invest. Oct. 2002;110(7):955-63.
Xie et al., Quantitative structure-activity relationship study of histone deacetylase inhibitors. Curr Med Chem Anticancer Agents. May 2004;4(3):273-99.
Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.
Yardley, Drug resistance and the role of combination chemotherapy in improving patient outcomes. Int J Breast Cancer. 2013;2013:137414. 15 pages.
Zaja et al., Bendamustine salvage therapy for T cell neoplasms. Ann Hematol. Sep. 2013;92(9):1249-54.
Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.
Zhao et al., Comparison of methods for evaluating drug-drug interaction. Front Biosci (Elite Ed). Jan. 1, 2010;2:241-9.
Zhu et al., Histone deacetylase 3 implicated in the pathogenesis of children glioma by promoting glioma cell proliferation and migration. Brain Res. Jul. 3, 2013;1520:15-22.
Zinzani et al., Brentuximab Vedotin in Transplant-Naïve Relapsed/Refractory Hodgkin Lymphoma: Experience in 30 Patients. Oncologist. Dec. 2015;20(12):1413-6.
Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy.dose.escalation.of.tinostamustine.in.patients.with.relapsed.html?f=listing-3*browseby=8*sortby=1*media=1. 1 page, poster presentation. Jun. 1, 2019.
Zulkowski et al., Regression of brain metastases from breast carcinoma after chemotherapy with bendamustine. J Cancer Res Clin Oncol. Feb. 2002;128(2):111-3.
U.S. Appl. No. 13/143,155, filed Jul. 1, 2011, U.S. Pat. No. 8,609,864.
U.S. Appl. No. 14/075,145, filed Nov. 8, 2013, U.S. Pat. No. 9,096,627.
U.S. Appl. No. 14/972,750, filed Dec. 17, 2015, Re. 46,144.
U.S. Appl. No. 14/345,562, filed Nov. 3, 2014, U.S. Pat. No. 9,376,395.
U.S. Appl. No. 14/374,995, filed Jul. 28, 2014, U.S. Pat. No. 10,118,901.
U.S. Appl. No. 15/290,546, filed Oct. 11, 2016, 2018-0098969.
U.S. Appl. No. 15/290,546, filed Nov. 28, 2016, 2017-0151218.
U.S. Appl. No. 15/985,097, filed May 21, 2018, U.S. Pat. No. 10,406,138.
U.S. Appl. No. 16/517,936, filed Jul. 22, 2016, 2019-0343807.
U.S. Appl. No. 17/212,765, filed Mar. 25, 2021, 2021-0346351.
U.S. Appl. No. 15/314,167, filed Nov. 28, 2016, U.S. Pat. No. 9,993,482.
U.S. Appl. No. 15/314,172, filed Nov. 28, 2016, U.S. Pat. No. 11,419,853.
U.S. Appl. No. 17/874,621, filed Jul. 27, 2022, Pending.
U.S. Appl. No. 15/314,180, filed Nov. 28, 2016, U.S. Pat. No. 10,744,120.
U.S. Appl. No. 16/983,458, filed Aug. 3, 2020.

(56) References Cited

OTHER PUBLICATIONS

U.S. Appl. No. 16/994,154, filed Aug. 14, 2020, 2021-0059989.
U.S. Appl. No. 16/341,089, filed Apr. 11, 2019, U.S. Pat. No. 11,266,631.
U.S. Appl. No. 17/679,308, filed Feb. 24, 2022, Pending.
U.S. Appl. No. 16/621,885, filed Dec. 12, 2019, 2020-0113870.
U.S. Appl. No. 16/621,893, filed Dec. 12, 2019, 2020-0261423.
U.S. Appl. No. 16/621,896, filed Dec. 12, 2019, U.S. Pat. No. 11,413,276.
U.S. Appl. No. 17/885,696, filed Aug. 11, 2022, Pending.
U.S. Appl. No. 16/621,898, filed Dec. 12, 2019, U.S. Pat. No. 11,318,117.
U.S. Appl. No. 17/414,797, filed Jun. 16, 2021, 2022-0016084.
U.S. Appl. No. 17/414,806, filed Jun. 16, 2021, 2022-016085.
Bijnsdorp et al., Analysis of Drug Interactions. Cancer Cell Culture, Methods and Protocols, Second Edition, Methods in Molecular Biology, vol. 731. Ian A. Cree (Ed.), Humana Press. Chapter 34, pp. 421-434, (2011).
Chou, Drug combination studies and their synergy quantification using the Chou-Talalay method. Cancer Res. Jan. 15, 2010;70(2):440-6.
Gemmill et al., Synergistic growth inhibition by Iressa and Rapamycin is modulated by VHL mutations in renal cell carcinoma. Br J Cancer. Jun. 20, 2005;92(12):2266-77.
Lin et al., The antiproliferative effect of C2-ceramide on lung cancer cells through apoptosis by inhibiting Akt and NF? B. Cancer Cell Int. Jan. 6, 2014;14(1):1, 7 pages.
Palmer et al., Combination Cancer Therapy Can Confer Benefit via Patient-to-Patient Variability without Drug Additivity or Synergy. Cell. Dec. 14, 2017;171(7):1678-1691.

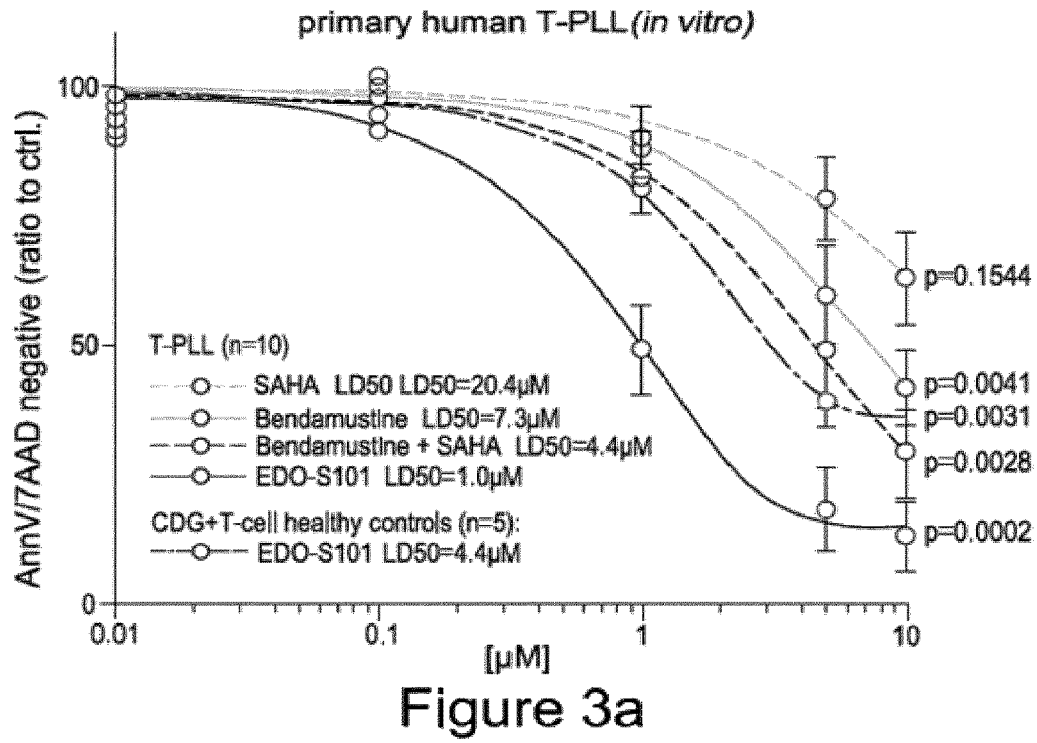
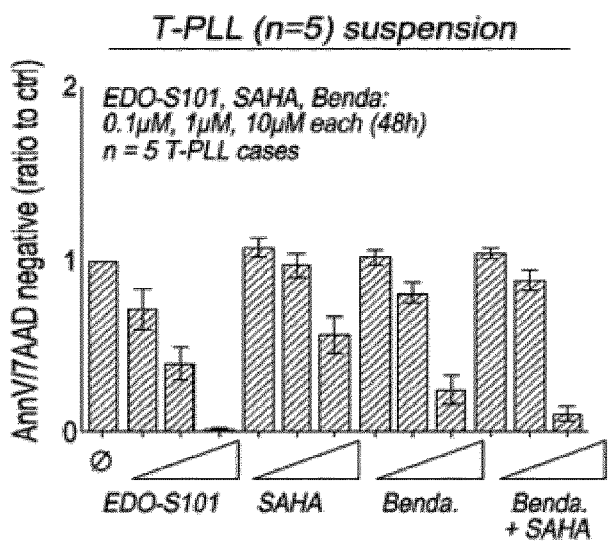
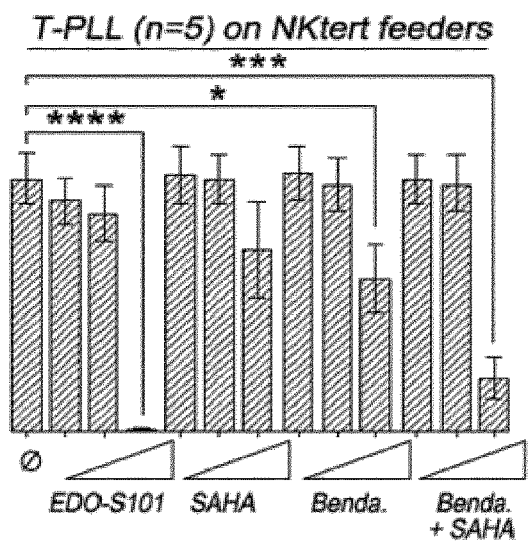
Figure 3a
Figure 3b
Figure 3c

TINOSTAMUSTINE FOR USE IN THE TREATMENT OF T-CELL PROLYMPHOCYTIC LEUKAEMIA

CROSS-REFERENCE TO RELATED APPLICATIONS

This application is a continuation application of U.S. patent application Ser. No. 16/621,898, filed on Dec. 12, 2019, which is a U.S. national stage application filed under 35 U.S.C. 371 based on International Patent Application No. PCT/EP2018/065664, filed on Jun. 13, 2018, which claims priority to Great Britain Application No. 1709402.0, filed on Jun. 13, 2017. The contents of each of the aforementioned applications are herein incorporated by reference in their entities.

TECHNICAL FIELD

The present invention relates to a method of treating T-cell prolymphocytic leukemia (T-PLL).

BACKGROUND TO THE INVENTION

Cancer is one of the most life threatening diseases. Cancer is a condition in which cells in a part of the body experience out-of-control growth. According to latest data from American Cancer Society, it is estimated there will be 1.69 million new cases of cancer in USA in 2017. Cancer is the second leading cause of death in the United States (second only to heart disease) and will claim more than 601,000 lives in 2017. In fact, it is estimated the average lifetime risk of developing cancer is 40.8% for American males and 37.5% for American women. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

For decades surgery, chemotherapy, and radiation were the established treatments for various cancers. Patients usually receive a combination of these treatments depending upon the type and extent of their disease. But chemotherapy is the most important option for cancer patients when surgical treatment (i.e. the removal of diseased tissue) is impossible. While surgery is sometimes effective in removing tumours located at certain sites, for example, in the breast, colon, and skin, it cannot be used in the treatment of tumours located in other areas, such as the backbone, nor in the treatment of disseminated hematologic cancers include cancers of the blood and blood-forming tissues (such as the bone marrow). They include multiple myeloma, lymphoma and leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by the cancer cells, a serious problem that may lead to recurrence of disease or even death. Thus, more effective cancer treatments are needed.

Leukemia is a cancer of the blood cells. Leukemias begin in the blood-forming tissue of the bone marrow. The cancers do not form solid tumours but instead large numbers of abnormal white blood cells (leukemia cells and leukemic blast cells) build up in the blood and bone marrow. There are four main types of leukemia: Acute myeloid leukemia (AML), Chronic myeloid leukemia (CML), Acute lymphocytic leukemia (ALL), and Chronic lymphocytic leukemia (CLL).

T-cell prolymphocytic leukemia (T-PLL) is recognised in the WHO classification of hematologic malignancies as a leukemic peripheral T-cell neoplasm and is of mature T-cell phenotype. Although representing the most frequent mature T-cell leukemia, T-PLL is nevertheless an extremely uncommon hematological malignancy and is rarely encountered in daily routine (with incidence of ~0.6/million). T-PLL also has a very poor prognosis, with the median overall survival of patients with T-PLL being around 7 months with conventional chemotherapy.

Patients with T-PLL typically present with exponentially rising lymphocyte counts in peripheral blood accompanied by lymphadenopathy with hepatosplenomegaly, and bone marrow involvement.

T-PLL characteristically shows rapid progression and does not respond well to standard multi-agent chemotherapy. The monoclonal anti-CD52 antibody alemtuzumab was the only (targeted) agent that was shown to induce a high rate of remission, albeit with relapse the rule. Alemtuzumab had overall response rates ranging from 51-95% with a median survival of 15-19 months in patients achieving a complete response.

However, alemtuzumab was withdrawn from the market in 2012 and there is currently no effective first line treatment for T-PLL.

There is therefore a need for effective chemotherapeutic treatments of T-PLL.

In WO-A-2010/085377, the compound of formula I below is disclosed. It is a first-in-class dual-functional alkylating-HDACi fusion molecule which potently inhibits the HDAC pathway.

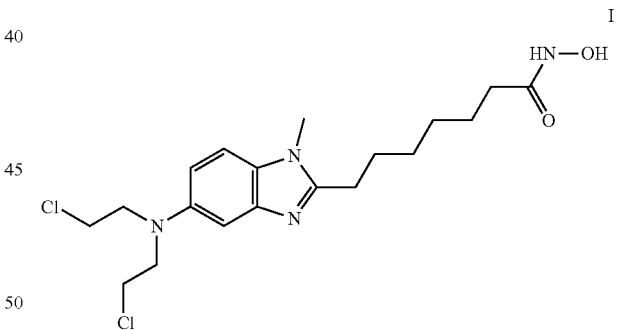

Biological assays showed that the compound of formula I potently inhibits HDAC enzyme (HDAC1 $IC_{50}$ of 9 nM). The compound of formula I has an INN of tinostamustine and is also known in the art as EDO-S101. It is an AK-DAC (a first-in-class alkylating deacetylase molecule) that, in preclinical studies, has been shown to simultaneously improve access to the DNA strands within cancer cells, break them and block damage repair.

SUMMARY OF THE INVENTION

In a first aspect of the present invention there is provided tinostamustine or a pharmaceutically acceptable salt thereof for use in the treatment of T-cell prolymphocytic leukemia (T-PLL).

It has surprisingly been discovered that tinostamustine or a pharmaceutically acceptable salt thereof is particularly effective in the treatment of T-PLL, with activity data showing strong in vitro and in vivo sensitivity to this compound. Thus, the need for a new and effective treatment of T-PLL is met by the present invention.

In a further aspect of the present invention there is provided use of tinostamustine or a pharmaceutically acceptable salt thereof for the manufacture of a medicament for the treatment of T-PLL.

In a further aspect of the present invention there is provided a method of treating T-PLL in a patient in need thereof comprising administering to said patient an effective amount of tinostamustine or a pharmaceutically acceptable salt thereof.

In a further aspect of the present invention there is provided a kit comprising tinostamustine or a pharmaceutically acceptable salt thereof together with instructions for treating T-PLL.

The following features apply to all aspects of the invention.

DETAILED DESCRIPTION OF THE INVENTION

Figure 1A:
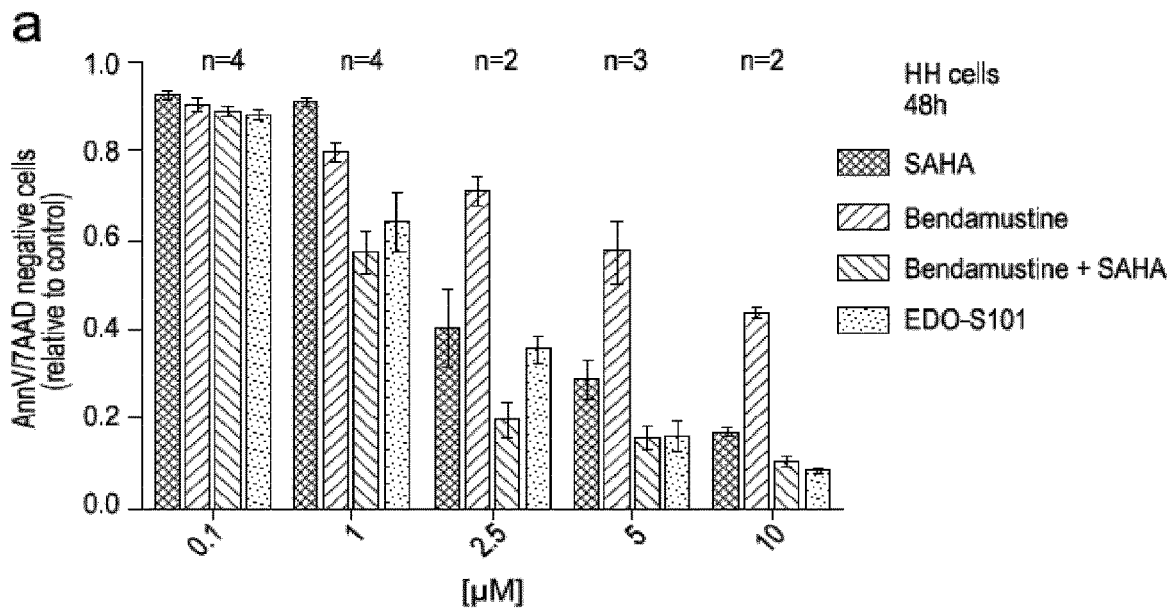
FIG. 1a shows a plot of HH cell viability relative to control after exposure to increasing concentrations of the HDAC inhibitor SAHA (vorinostat), bendamustine, SAHA+bendamustine, and EDO-S101.

In the present application, a number of general terms and phrases are used, which should be interpreted as follows.

The compound of formula I has an INN of tinostamustine and is also known in the art as EDO-S101. The IUPAC name is 7-(5-(bis(2-chloroethyl)amino)-1-methyl-1H-benzo[d]imidazol-2-yl)-N-hydroxyheptanamide.

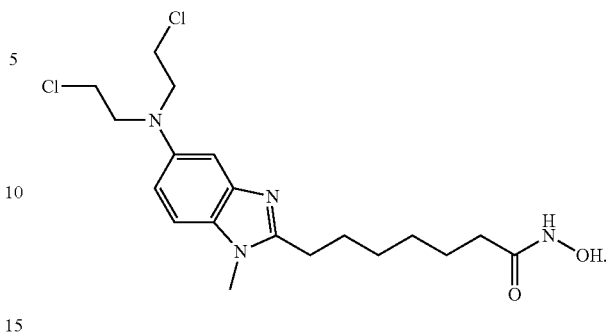

"Patient" includes humans, non-human mammals (e.g., dogs, cats, rabbits, cattle, horses, sheep, goats, swine, deer, and the like) and non-mammals (e.g., birds, and the like).

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonae, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

In the present invention, the pharmaceutically acceptable salt of tinostamustine may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, oxalate, succinate, fumarate, tartrate, tosylate, mandelate, salicylate, lactate, p-toluenesulfonate, naphthalenesulfonate or acetate salt.

It has been found that tinostamustine or a pharmaceutically acceptable salt thereof shows surprising efficacy in T-PLL. In particular, it has been found that tinostamustine or a pharmaceutically acceptable salt thereof is useful in the treatment of T-PLL.

T-cell prolymphocytic leukemia or T-PLL is a leukemic peripheral T-cell neoplasm and is of mature T-cell phenotype (Campo, E et al, Blood 117, 2011 5019-32). Although representing the most frequent mature T-cell leukemia, T-PLL is nevertheless an extremely uncommon hematological malignancy and is rarely encountered in daily routine (with incidence of ~0.6/million). T-PLL also has a very poor prognosis, with the median overall survival of patients with T-PLL being around 7 months with conventional chemotherapy.

Patients with T-PLL typically present with exponentially rising lymphocyte counts in peripheral blood accompanied by lymphadenopathy with hepatosplenomegaly, and bone marrow involvement.

The therapeutically effective amount of tinostamustine or a pharmaceutically acceptable salt administered to the patient is an amount which confers a therapeutic effect in accordance with the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of tinostamustine or a pharmaceutically acceptable salt thereof according to the present invention is believed to be one wherein tinostamustine or a pharmaceutically acceptable salt thereof is included at a dosage range of from 0.3 mg/m$^2$ to 300 mg/m$^2$ body surface area of the patient or from 20 mg/m$^2$ to 150 mg/m$^2$ body surface area of the patient.

The specific therapeutically effective dose level for any particular patient will depend upon a variety of factors including the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

"Metastatic Cancer". Cancer has the ability to spread within the body. Cancer cells can spread locally by moving into nearby normal tissue. Cancer can also spread regionally, to nearby lymph nodes, tissues, or organs. Cancer can therefore spread to distant parts of the body. When this happens, it is called metastatic cancer (also known as stage IV cancer), and the process by which cancer cells spread to other parts of the body is called metastasis. Thus, in metastasis, cancer cells break away from where they first formed (primary cancer), travel through the blood or lymph system, and form new tumours (metastatic tumours) in other parts of the body.

Metastatic cancer cells have features like that of the primary cancer and not like the cells in the place where the cancer is found. This enables doctors to tell whether a cancer is metastatic. Metastatic cancers are given the same name as the primary cancer. For example, breast cancer that has spread to the lung is called metastatic breast cancer, not lung cancer. It is treated as stage IV breast cancer, not as lung cancer.

Metastatic T-PLL refers to a T-cell prolymphocytic leukemia that has metastasised to a new location in the body. The cancer is treated as a stage IV T-PLL cancer.

"Advanced Cancer" is a cancer that is not curable but responds to treatment. Disease directed therapy is still very important because it prolongs life. For terminal cancer, therapy cannot prolong survival significantly due to the progressive nature of the disease and palliative care is the main treatment option.

Suitable examples of the administration form of tinostamustine or a pharmaceutically acceptable salt thereof include without limitation oral, topical, parenteral, sublingual, rectal, vaginal, ocular, and intranasal. Parenteral administration includes subcutaneous injections, intravenous, intramuscular, intrasternal injection or infusion techniques. Preferably, tinostamustine or a pharmaceutically acceptable salt thereof is administered parenterally, and most preferably intravenously.

Preferably, tinostamustine or a pharmaceutically acceptable salt thereof is administered intravenously to the patient in need thereof at a dosage level to the patient in need thereof of from 0.3 mg/m$^2$ to 300 mg/m$^2$ body surface area of the patient.

Preferably, tinostamustine or a pharmaceutically acceptable salt thereof is administered intravenously to the patient in need thereof at a dosage level to the patient in need thereof of from 20 mg/m$^2$ to 150 mg/m$^2$ body surface area of the patient.

It has been found that in embodiments of the present invention, tinostamustine or a pharmaceutically acceptable salt thereof or medicament comprising the same may preferably be administered to a patient in need thereof on day 1 of each treatment cycle.

Tinostamustine or a pharmaceutically acceptable salt thereof may be administered on day 1 of a 21 day treatment cycle.

In embodiments according to the present invention, tinostamustine or a pharmaceutically acceptable salt thereof or medicament comprising the same is administered to a patient in need thereof over an infusion time of 60 minutes; or an infusion time of 45 minutes; or an infusion time of 30 minutes.

In embodiments according to the present invention, tinostamustine or a pharmaceutically acceptable salt is administered to the patient in need thereof at a dosage level of from 20 mg/m$^2$ to 150 mg/m$^2$ body surface area of the patient, on day 1 of a 21 day treatment cycle, over an infusion time of 60 minutes.

In embodiments of the present invention, there is provided a kit comprising tinostamustine or a pharmaceutically acceptable salt thereof together with instructions for treating T-PLL.

The instructions may advise administering tinostamustine or a pharmaceutically acceptable salt thereof according to variables such as the state of the T-PLL being treated; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts.

In a further embodiment of the present invention, the patient in need of said treatment is given radiotherapy with (including prior to, during or after) treatment of the T-PLL with tinostamustine or a pharmaceutically acceptable salt thereof. In embodiments of the present invention, the patient is treated with tinostamustine or a pharmaceutically acceptable salt thereof and radiotherapy. Preferably, the patient is given radiotherapy treatment prior to the treatment with tinostamustine or a pharmaceutically acceptable salt thereof. The radiotherapy may be given at a dose of 1 to 5 Gy over 5-10 consecutive days and preferably 2 Gy over 5-10 consecutive days.

In a further embodiment of the present invention, the patient in need of said treatment is given radiotherapy prior to or after treatment of the T-PLL with tinostamustine or a pharmaceutically acceptable salt thereof. Preferably, the patient is given radiotherapy treatment prior to the treatment with tinostamustine or a pharmaceutically acceptable salt thereof. The radiotherapy may be given at a dose of 1 to 5 Gy over 5-10 consecutive days and preferably 2 Gy over 5-10 consecutive days.

When intended for oral administration, tinostamustine or a pharmaceutically acceptable salt thereof or medicament comprising the same may be in solid or liquid form, where semi-solid, semi-liquid, suspension and gel forms are included within the forms considered herein as either solid or liquid.

Tinostamustine or a pharmaceutically acceptable salt thereof or medicament comprising the same can be prepared for administration using methodology well known in the pharmaceutical art. Examples of suitable pharmaceutical formulations and carriers are described in "Remington's Pharmaceutical Sciences" by E. W. Martin.

As a solid composition for oral administration, tinostamustine or a pharmaceutically acceptable salt thereof can be formulated into a powder, granule, compressed tablet, pill, capsule, chewing gum, wafer or the like form. Such a solid composition typically contains one or more inert diluents or carriers. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When tinostamustine or a pharmaceutically acceptable salt thereof compositions is in the form of a capsule (e.g. a gelatin capsule), it can contain, in addition to materials of the above type, a liquid carrier such as polyethylene glycol, cyclodextrin or a fatty oil.

Tinostamustine or a pharmaceutically acceptable salt thereof compositions can be in the form of a liquid, e.g. an elixir, syrup, solution, emulsion or suspension. The liquid can be useful for oral administration or for delivery by injection. When intended for oral administration, tinostamustine or a pharmaceutically acceptable salt thereof compositions can comprise one or more of a sweetening agent, preservatives, dye/colorant and flavor enhancer. In tinostamustine or a pharmaceutically acceptable salt thereof compositions for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, tinostamustine or a pharmaceutically acceptable salt thereof or medicament comprising the same is administered intravenously.

Liquid forms of tinostamustine or a pharmaceutically acceptable salt thereof or medicament comprising the same, may be solutions, suspensions or other like form, and can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

Tinostamustine or a pharmaceutically acceptable salt thereof or medicament comprising the same can be administered by any convenient route, for example by infusion or bolus injection, by absorption through epithelial or mucocutaneous linings, and preferably by bolus.

Examples of compositions comprising tinostamustine or a pharmaceutically acceptable salt thereof are disclosed in WO2013/040286.

The present invention may be further understood by consideration of the following non-limiting examples.

EXAMPLES

In the following examples, the compound having the following formula I is referred to as EDO-S101.

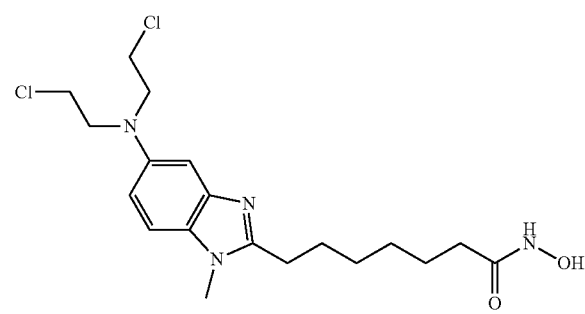

EDO-S101 may be prepared as described in Example 6 of WO-A-2010/085377.

Materials and Methods

EDO-S101 and Control Compounds

EDO-S101 was provided by EDO MundiPharma, and synthesised as described in Example 6 of WO-A-2010/085377.

Bendamustine was provided by EDO MundiPharma.

Vorinostat (SAHA) (catalogue reference number SML0061-5 mg) and Fludarabine were purchased from Sigma-Aldrich.

Cell Culture

RPMI-1640 medium (Sigma-Aldrich) supplemented with 1% L-Glutamine (200 mM; Sigma-Aldrich), 10% fetal bovine serum (FBS) (Sigma-Aldrich) and Penicillin/Streptomycin (100 U/0.1M; PAA) was used for in-vitro experimentation on suspension cultures of primary T-PLL cells, healthy CD3+ T cells, HH cells, and in co-culture experiments with NKtert cells. Cell suspensions were maintained at a density of $1.0 \times 10^6$ cells/mL (primary T-PLL cells) and $2.5 \times 10^5$ cells/mL (HH cells) for all cell culture experiments.

Cells were cultured in a HERAcell incubator (Thermo Scientific Heraeus) at 37° C. and 5% $CO_2$ with 90% humidity. CD4+ mature T-cell leukemia HH cells were originally isolated from a patient with Sézary Syndrome (Starkebaum et al., 1991). NKtert (human bone marrow stromal cells [BMSC]) were purchased from RIKEN Cell Bank in 2011. Only cells derived from the original cell stock as purchased, and which had been propagated for 2 to 3 passages before long-term storage in liquid nitrogen, were used. Cell cultures were terminated after the $10^{th}$ passage (4 to 6 weeks of being in culture). Cells were authenticated following thawing by evaluation of characteristic growth behaviour and by flow cytometry. Cells were routinely tested for the presence of mycoplasma, using standard PCR protocols (primers: for1: 5'-acaccatgggagytggtaat-3', (SEQ ID No; 1) rev1: 5'-cttcwtc-gattycagacccaaggcat-3 (SEQ ID NO: 2)', for2: 5'-gtgsggmtggatcacctcct-3 (SEQ ID NO: 3)', rev2: 5'-gcatc-caccawawacyctt-3'(SEQ ID NO: 4)).

Healthy CD3+ T-cells were isolated from healthy human donors.

For co-culture experiments human bone marrow stromal cells (BMSC) NKtert cells (RIKEN BRC, Japan) were seeded at concentrations of $1.5 \times 10^4$ cells/well (96 well plate) and incubated at 37° C. in 5% $CO_2$. After 24 hours, NKtert cells at approximately 60-80% confluency were treated with 0.02 mg/mL Mitomycin C for 3 hours in RPMI-1460, and then washed twice with PBS (Life Technologies). After another 24 hours, $4 \times 10^5$ T-PLL cells were added per well (with and without feeder cell support) and treated for 48 hours with the indicated compounds.

In Vitro Drug Treatment and Cell Viability

EDO-S101 (EDO MundiPharma), and vorinostat (SAHA; SML0061-5 mg, Sigma-Aldrich) were dissolved in DMSO. The alkylating agent bendamustine (MundiPharma) was dissolved in methanol. Cells were treated with each compound (or compounds) at the indicated concentrations and times. Dosing was based on published ranges and $IC_{50}/LD_{50}$ titrations. Cell apoptosis was determined using dual staining for Annexin-V (AnxV) and 7AAD via flow cytometry.

Human primary T-PLL cells are unsuitable for cultivation under standard laboratory cell culture conditions, in part, due to their high levels of genomic heterogeneity and variable phenotypes. HH cells are derived from a highly chemotherapy resistant cutaneous lymphoma, and are suitable for cultivation under laboratory conditions. HH cells exhibit a comparable phenotype to T-PLL cells, and are therefore frequently used as a surrogate cell line for T-PLL cells for in vitro experiments. HH cells were therefore selected for the in vitro validation of EDO-S101.

Murine Models

DBA2xC57B6JF1 mice were used as recipients in all experiments. Transplantable leukaemia/lymphoma cells derived from CD2-MTCP1p13 tg mice (Gritti et al, Blood 1998, 92, 268-73; blood, spleen, and bone marrow) were intraperitoneally injected into background-matched mice (to facilitate the generation of uniform cohorts). $1 \times 10^7$ cells from CD2-MTCP1p13 mice were intraperitoneally injected into syngeneic recipients (n=26). Starting on day 10 post-transplantation, mice with a homogeneous distribution of leukemic blood leukocytes (WBC) were selected and randomly assigned into four treatment groups. Each group was then treated with either vehicle control (DMSO), fludarabine (34 mg/kg days 10, 15, 17, 21), bendamustine (day 10 at 60 mg/kg, days 15, 17, 21 at 20 mg/kg), and EDO-S101 (day 10 at 50 mg/kg, days 15, 17, 21 at 20 mg/kg) on the indicated days at the indicated doses.

Transplantable leukaemia/lymphoma cells derived from ΔJAK1 mice (Heinrich et al, Mol. Ther. 2013, 21, 1160-8; nodal/spleen mature T-cell lymphoma based on insertional mutagenesis activating JAK1) were intravenously injected into background-matched mice (to facilitate the generation of uniform cohorts). $2.5 \times 10^6$ cells were transplanted intravenously into Rag1-deficient mice. Recipients of comparable leukocyte counts were then randomly divided into four treatment groups. Each treatment group was thenh treated with 18 mg/kg of either bendamustine, fludarabine, EDO-S101, or with vehicle control on days 7, 10, 13, 17, 22 (DMSO).

Patient Samples

T-PLL cells were isolated from peripheral blood (PB) of T-PLL patients diagnosed according to WHO criteria (Swerdlow, S. H. et al Blood 2016, 127, 2375-90; Herling et al Blood 2004, 104, 328-335). Diagnosis was based on clinical features, immunophenotyping (flow-cytometry and histochemistry; including TCL1A/MTCP1 expression), FISH/karyotypes, and molecular studies (TCRmonoclonality). Human tumour samples were obtained under institutional review board (IRB)-approved protocols following written informed consent according to the Declaration of Helsinki. Collection and use was approved for research purposes by the ethics committee of the University Hospital of Cologne (#11-319). The patient cohort was selected based on uniform front-line treatment (87% of cases) with either single-agent alemtuzumab or fludarabine-mitoxantrone-cyclophosphamide (FMC) plus alemtuzumab chemoimmunotherapy as part of the TPLL120 (NCT00278213) and TPLL2 (NCT01186640, unpublished) prospective clinical trials or as included in the nation-wide T-PLL registry (IRB #12-146) of the German CLL Study Group. At diagnosis, patients had a median age of 62 years and included 1.5-times more men than women. FISH analysis used standard protocols (Vysis, Abbott).

Western Blot Analysis

T-PLL cells were isolated from peripheral blood (PB) of T-PLL patients. T-PLL cells were cultured in suspension, and treated with either bendamustine (1 μM), vorinostat (1 μM), EDO-S101 (1 μM) or an equimolar combination of vorinostat/bendamustine (1 μM) for 36 hours at the indicated concentrations. After this time, the cells were harvested and lysed, the cell lysate sonicated, centrifuged to remove any cellular debris, and the supernatant collected. The protein concentration of each cell lysate solution (the supernatant) was determined and the western blot performed using standard methods.

The antibodies used were acHistone 3 (Sigma Aldrich), phospho-ATM Serine1981 (Sigma Aldrich), ATM (Sigma Aldrich), phospho-KAP-1 Serine824 (Sigma Aldrich), KAP-1 (Sigma Aldrich), phosphor-p53 Serine15 (Sigma Aldrich), acetyl-p53 (Sigma Aldrich), p53 (Sigma Aldrich), PARP (Sigma Aldrich), cleaved-PARP (Sigma Aldrich), and β-Actin (Sigma Aldrich).

Example 1—Cell Viability

To evaluate the cytotoxicity of EDO-S101 in comparison to bendamustine and vorinostat (SAHA), HH cells were treated with either EDO-S101, bendamustine, vorinostat or an equimolar bendamustine/vorinostat combination over a period 48 hours. Cells were treated with either 0.1 μM, 1 μM, 2.5 μM, 5 μM or 10 μM solutions of the indicated compounds (FIG. 1a).

Figure 1B:
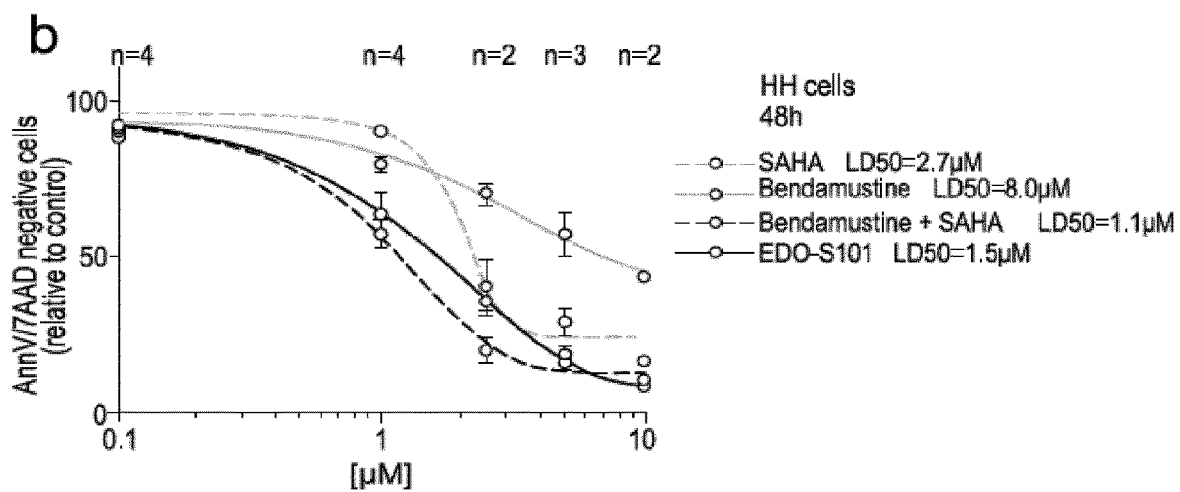
FIG. 1b shows a dose response curve for the SAHA (vorinostat), bendamustine, SAHA+bendamustine, and EDO-S101, in HH cells.

Following treatment, cell death was evaluated by staining cells with the apoptosis markers Annexin-V and 7-AAD, and the number of apoptotic cells quantified by flow cytometry. Annexin-V specifically targets and identifies apoptotic cells. 7-AAD is a marker of late stage apoptotic, or necrotic cells. The number of Annexin-V and 7-AAD negative cells was counted for each sample. Each experiment was repeated for the indicated number of times, and the average number of apoptosis negative cells plotted and normalised relative to an untreated control sample (FIG. 1a). A dose response curve (FIG. 1b) for each treatment was subsequently plotted, and the $LD_{50}$ (median lethal dose) of each treatment determined.

The equimolar combination of bendamustine and vorinotstat ($LD_{50}$: 1.1 µM), and EDO-S101 ($LD_{50}$: 1.5 µM) demonstrated marked potency in HH cell death induction after 48 hours of treatment. Both the bendamustine/vorinostat combination and EDO-S101 exhibited $LD_{50}$ values in the low micromolar range. Furthermore, both EDO-S101 and the bedamustine/vorinostat combination treatment demonstrated enhanced cytotoxicity compared to vorinostat ($LD_{50}$: 2.7 µM) and bendamustine ($LD_{50}$: 8.0 µM) as single agents.

Example 2—Western Blot Analysis of Patient T-PLL Samples

T-PLL cells (ATM mutated at L1238*, mono-allelic ATM loss, copy no=1.41) were isolated from peripheral blood (PB) of T-PLL patients were cultured in suspension, and treated with 1 µM of either bendamustine (FIG. 2, lane 2), vorinostat (lane 3), EDO-S101 (lane 5) or an equimolar combination of vorinostat/bendamustine (lane 4) for 36 hours. After this time, the cells were harvested, lysed and protein expression levels determined by western blot analysis.

Figure 2:
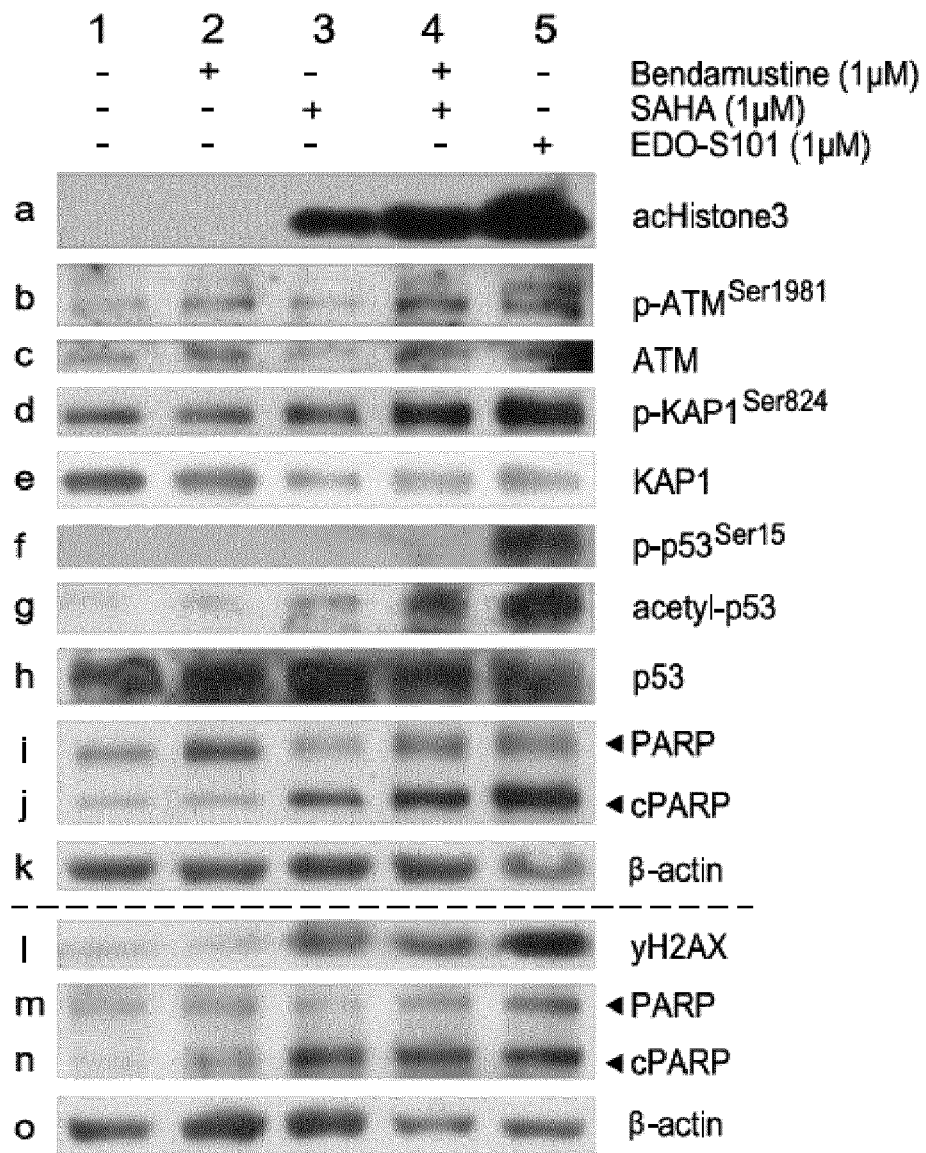
FIG. 2 shows western blots analysis of patient T-PLL samples showing the effect of SAHA (vorinostat), bendamustine, SAHA+bendamustine, and EDO-S101 on various markers relevant to T-PLL.

FIG. 2 shows western blots of the cell lysate for each treatment, compared to a negative control (lane 1). Staining for β-Actin was used as a loading control for each western blot ran (rows a to k, and rows l to o respectively).

HDAC inhibitors target proteins which promote the deacetylation of histones, or the deacetylation of other proteins. Acetylation and deacetylation of histones are post-translational modifications implicated in DNA replication and repair, and therefore the acetylation status of histones is crucial in cell replication pathways. Inhibition of HDAC activity is therefore linked to induction of the DNA damage response. HDAC inhibitors used in these experiments include vorinostat and the fusion molecule EDO-S101.

DNA alkylating agents prevent normal DNA replication pathways from functioning by binding to DNA, and therefore cause replication stress. In an attempt to repair the damage caused, the cell recruits an array of proteins, in what is referred to as the DNA Damage response (DDR). Many of the proteins recruited in the DDR may be used as biomarkers for damage and replication stress. Such biomarkers include increased expression levels of γH2AX, phosphorylated ATM (pATM), phosphorylated Kap1 (pKap1), and stabilisation of p53. DNA alkylating agents used in this example include bendamustine, and the fusion molecule EDO-S101 (which is also a HDAC inhibitor).

Referring to FIG. 2, it is clear that treatment of T-PLL cell samples isolated from patients with EDO-S101 led to the most significant induction of the DDR, compared to treatment with bendamustine, vorinostat or a combination thereof. Cells treated with EDO-S101 revealed the largest increase in levels of γH2AX (row l), pATM (row b), and pKAP1 (row d), all of which are heavily implicated in the DNA damage response. In line with the induction of the DDR, the expression levels of Kap1 (row e) were reciprocally related to the levels of pKap1. These results indicate that EDO-101 exhibits the most potent DNA alkylating activity compared to vorinostat and bendamustine, and furthermore, that EDO-S101 exceeds the potency of a combination of vorinostat and bendamustine.

The induction of the DDR also causes stabilization of p53 (row h) and subsequent phosphorylation (row f) and acetylation of p53 (acetyl-p53; row g). Referring to FIG. 2, treatment of cells with EDO-S101 resulted in the greatest accumulation of acetyl-p53 (row g) and p-p53 (row f), compared to bendamustine, vorinostat or a combination thereof. These results further support EDO-S101 being the most potent inducer of DNA damage.

Where DNA damage is extensive and the DNA cannot be repaired, p53 pathways are responsible for inducing cell apoptosis. One such pathway is characterized by the cleavage of PARP. As can be seen in FIG. 2, treatment of cells with EDO-S101 caused the greatest increase in cleaved PARP (cPARP; row j), compared to bendamustine, vorinostat, or a combination thereof. These data indicate that treatment with EDO-S101 caused the most extensive and irreparable DNA damage in T-PLL cells, promoting cell apoptosis. Furthermore, these data are indicative that treatment of T-PLL cells from patients with EDO-S101 effectively overcomes the protective effect conferred by stromal cells against cell apoptosis.

Referring to FIG. 2, treatment of T-PLL cells with EDO-S101 resulted in the largest increase in acetylation of histone3 (acHistone3), compared to vorinostat or a combination of vorinostat and bendamustine. These data indicate that EDO-S101 was a more effective HDAC inhibitor than vorinostat alone, or vorinostat in combination with bendamustine, in T-PLL cells.

In conclusion, FIG. 2 indicates that EDO-S101 induces the strongest DNA damage response in cells. This can be attributed to its enhanced potency as a DNA alkylator, and also as a HDAC inhibitor, compared to bendamustine or vorinostat. Furthermore, it is clear that the DNA damage and hyperacetylation induced by EDO-S101, exceeds that induced by a combination of vorinostat and bendamustine (see for example the comparably elevated levels of pATM, acetyl-p53, pKAP1, γH2AX and acHistone 3). As a result, apoptosis in strongly induced in EDO-S101 treated cells, compared to those treated with a combination of vorinostat and bendamustine (see elevated levels of cPARP).

Example 3—Induction of Apoptosis and Resistance of EDO-S101 Treated Cells to Stromal Cell Mediated Protection in T-PLL To further evaluate apoptosis in cells treated with EDO-S101, primary human T-PLL cells were treated with either vorinostat, bendamustine, EDO-S101, or an equimolar combination of vorinostat and bendamustine, at 0.01 µM, 0.1 µM, 1 µM, 5 µM or 10 µM concentrations, and incubated for 48 hours. Following treatment, cell death was evaluated by staining cells with the apoptosis markers Annexin-V and 7-AAD, and the number of apoptotic cells quantified by flow cytometry. Each experiment was repeated for the indicated number of times, and the average number of apoptosis negative cells plotted and normalised relative to an untreated control sample. A dose response curve (FIG. 3a) for each treatment was subsequently plotted, and the $LD_{50}$ (median lethal dose) of each treatment determined.

The $LC_{50}$ values for each treatment were calculated for vorinostat (20.4 µM), bendamustine (7.3 µM), EDO-S101 (1.0 µM), or an equimolar combination of vorinostat and bendamustine (4.4 µM). The $LC_{50}$ value for EDO-S101 was found to be lower in primary human T-PLL cells (1.0 µM) (FIG. 3a) than in HH cells (1.5 µM) (FIG. 1b) under comparable experimental conditions indicating enhanced efficacy against T-PLL cells. Furthermore, EDO-S101 (1.0 µM) exhibited approximately a 4-fold increase in potency against T-PLL cells compared to a combination of vorinostat and bendamustine (4.4 µM).

The $LC_{50}$ of EDO-S101 in healthy CD3+ T-cells was determined to be 4.4 µM, indicating that EDO-S101 was approximately 4-fold more potent against T-PLL cells compared to healthy CD3+ T-cells, under experimental conditions. This result demonstrated that EDO-S101 had selectivity for T-PLL cells over healthy T-cells.

NKtert bone-marrow stromal cells are known to protect mutated T-cells against the effects of drugs and against apoptosis. To evaluate the protections conferred by NKtert cells to primary human T-PLL cells, NKtert cells and T-PLL cells were co-cultured for treatment with EDO-S101. Primary T-PLL cells with (FIG. 3b) and without (FIG. 3c) co-cultures of NKtert cells were treated with increasing concentrations (0.1, 1, or 10 µM) of vorinostat, bendamustine, an equimolar combination of vorinostat and bendamustine, or EDO-S101, and incubated for 48 hours.

Following treatment, cell death was evaluated by staining cells with the apoptosis markers Annexin-V and 7-AAD, and the number of apoptotic cells quantified by flow cytometry. Each experiment was repeated for the indicated number of times, and the average number of apoptosis negative cells plotted as a ratio relative to an untreated control sample (FIG. 3b, FIG. 3c).

Referring to FIG. 3b, the control sample Ø on the left hand graph is normalised to 1 for normal T-PLL cells. As can be seen from FIG. 3c the control sample Ø for the T-PLL/NKtert co-cultured cells is greater than 1, indicating enhanced survival of T-PLL cells in the presence of NKtert cells compared to monoculture.

Referring to FIGS. 3b and 3c, both T-PLL cells, and T-PLL/NKtert co-cultured cells, were sensitive to treatment with EDO-S101. Extensive apoptosis was observed in both T-PLL cells, and co-cultured T-PLL/NKtert cells, when treated with 10 µM EDO-S101, with an approximate cell death count of greater than 95%. These data indicate that treatment of T-PLL cells with EDO-S101 overcame the protection conferred by the NKtert cells. Furthermore, T-PLL cells treated with either bendamustine, vorinostat, or an equimolar combination of bendamustine and vorinostat, were not as effective as EDO-S101 in overcoming NKtert associated protection co-cultured T-PLL cells. These data are further supported by the observation that treatment of human T-PLL cells with EDO-S101 led to the most enhanced levels of cPARP, a key indicator of cell apoptosis (FIG. 2).

Figure 3D:
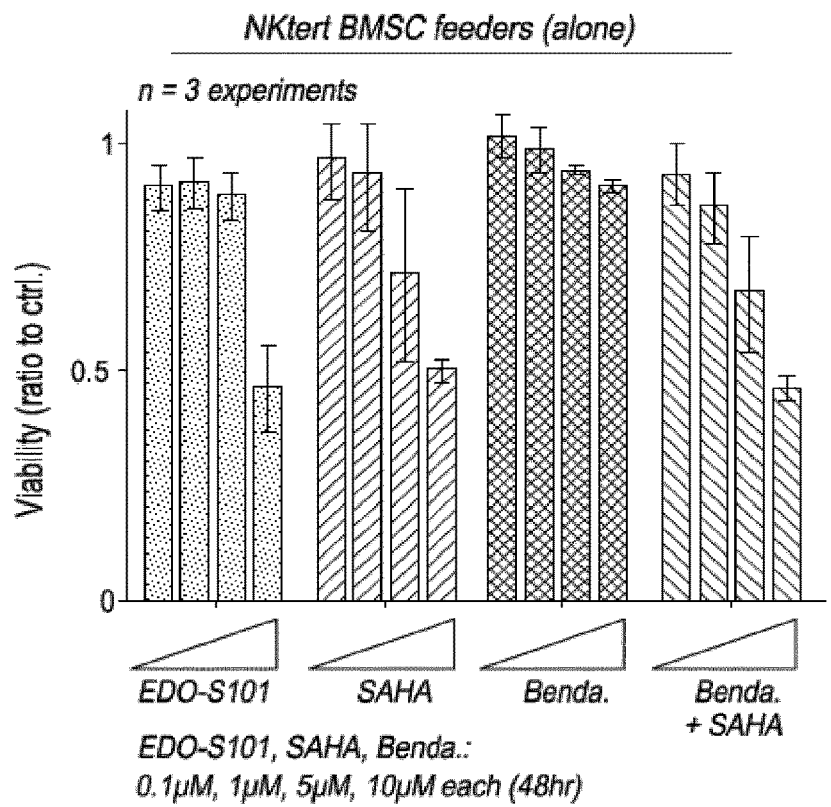
FIG. 3a is a dose response curve showing the relative number of living T-PLL cells in suspension culture after 48 h treatment comparing SAHA (vorinostat), bendamustine, SAHA+bendamustine, and EDO-S101.
FIG. 3b shows the effect of increasing concentrations of SAHA (vorinostat), bendamustine, SAHA+bendamustine, and EDO-S101, on primary T-PLL cells with and without co-cultures of the human bone marrow stromal cell line NKtert.
FIG. 3c shows the effect of increasing concentrations of SAHA (vorinostat), bendamustine, SAHA+bendamustine, and EDO-S101, on NKtert cell viability.

It was hypothesised that EDO-S101 could be affecting the viability of the NKtert cells in the co-cultured T-PLL/NKtert cell experiments shown in FIG. 3c. Consequently, the effect on cell viability of NKtert bone marrow stromal cells (BMSC) feeders cells alone was also investigated. Cells were treated with either bendamustine, vorinostat, an equimolar combination of bendamustine and vorinostat, or EDO-S101, at either 0.1, 1, 5 or 10 µM concentrations, incubated for 48 hours, and cell viability assessed using MTT assays (FIG. 3d). As can be seen in FIG. 3d, the reduction in viability of NKtert cells treated with EDO-S101, vorinostat, or an equimolar combination of vorinostat and bendamustine, were largely comparable over the concentrations investigated. Bendamustine treatment did not have a pronounced concentration dependent effect on the viability of NKtert cells. Importantly, the viability of cells treated with EDO-S101 and vorinostat at 10 µM were comparable, providing confidence that the cell death induced by treatment of T-PLL/NKtert co-cultured cells with EDO-S101 (FIG. 3c) was not a result of reduced viability of NKtert cells (FIG. 3d).

Example 4—In Vivo Analysis of Leukemic Blood Leukocytes (WBC) Count Following Treatment With EDO-S101

Figure 4A:
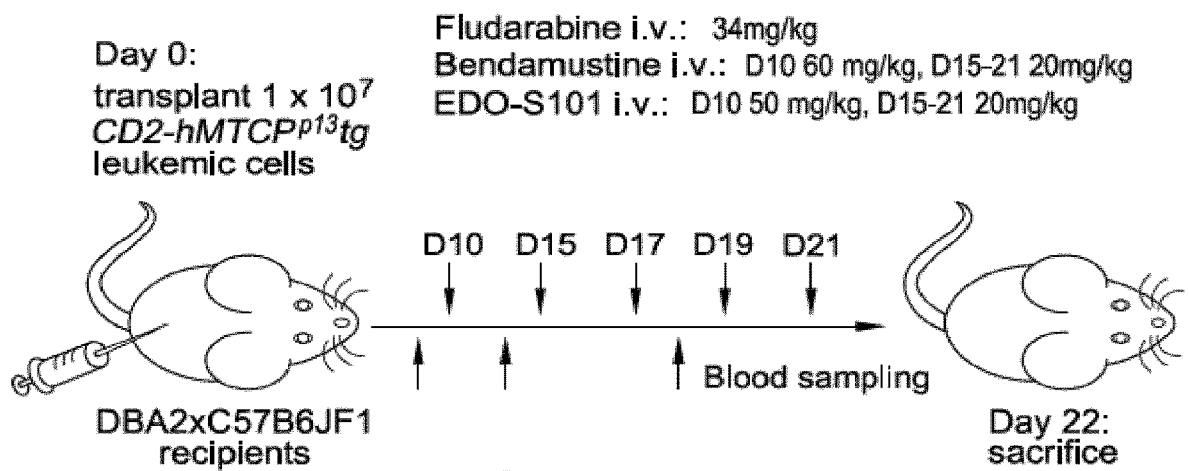
FIGS. 4a 4b and 4c show the results of a transfer model for CD2-MTCP1 p13 mice investigating fludarabine, bendamustine and EDO-S101.

Mice were injected with leukaemia cells derived from CD2-MTCP1 mice, as previously described (FIG. 4a).

CD2-MTCP1 cells are an aggressive, transplantable subline and are suitable for in vivo analysis as a T-PLL like model. At day 10 post-transplantation of CD2-MTCP1 cells by intraperitoneal injection, mice with comparable leukemic blood leukocytes (WBC) counts were divided into four groups at random. Each group was intravenously administered either fludarabine (34 mg/kg), bendamustine (Day 10, 60 mg/kg; Day 15-21, 20 mg/kg) or EDO-S101 (Day 10, 50 mg/kg; Day 15-21, 20 mg/kg) at the indicated doses on Day 10, Day 15, Day 17, Day 19 and Day 21 post-transplantation. Samples of blood were taken at regular intervals (Day 9 and Day 14 post-transplantation), and the mice sacrificed at 22 days post-transplantation (FIG. 4a).

Fludarabine was selected for experiments as a comparative compound, and is a FDA approved chemotherapy for the treatment of leukemia and lymphoma. Fludarabine is a purine derivative, and interferes with the replication of DNA. It is on the World Health Organisation's List of Essential Medicines.

Figure 4B:
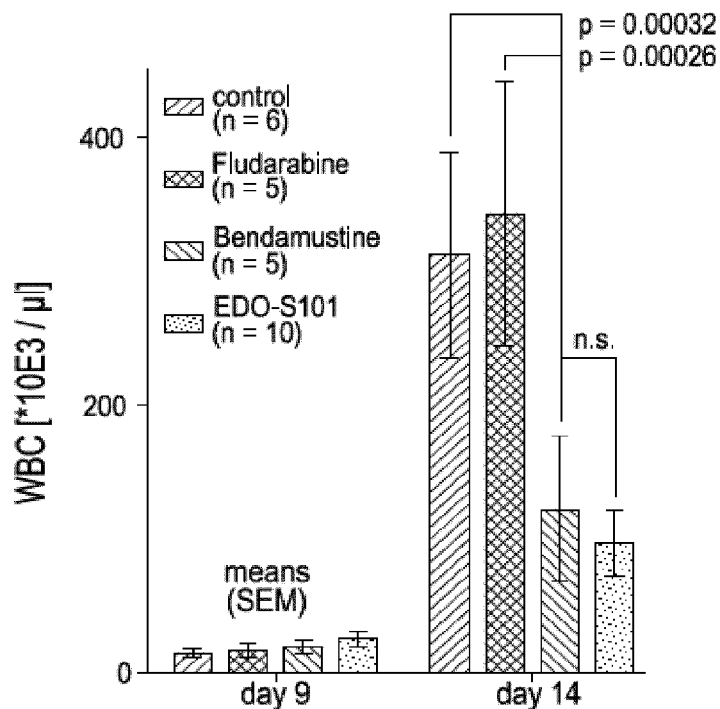

The blood samples taken were analysed for leukemic blood leukocyte levels (WBC), and the average cell count in each group determined. Comparison of WBC count at Day 14 and Day 9, revealed that bendamustine and EDO-S101 significantly delayed the increase in WBC cells compared to a control sample and fludarabine (FIG. 4b). These data indicated that EDO-S101 and bendamustine was delaying the onset of disease progression in the recipient mice.

Figure 4C:
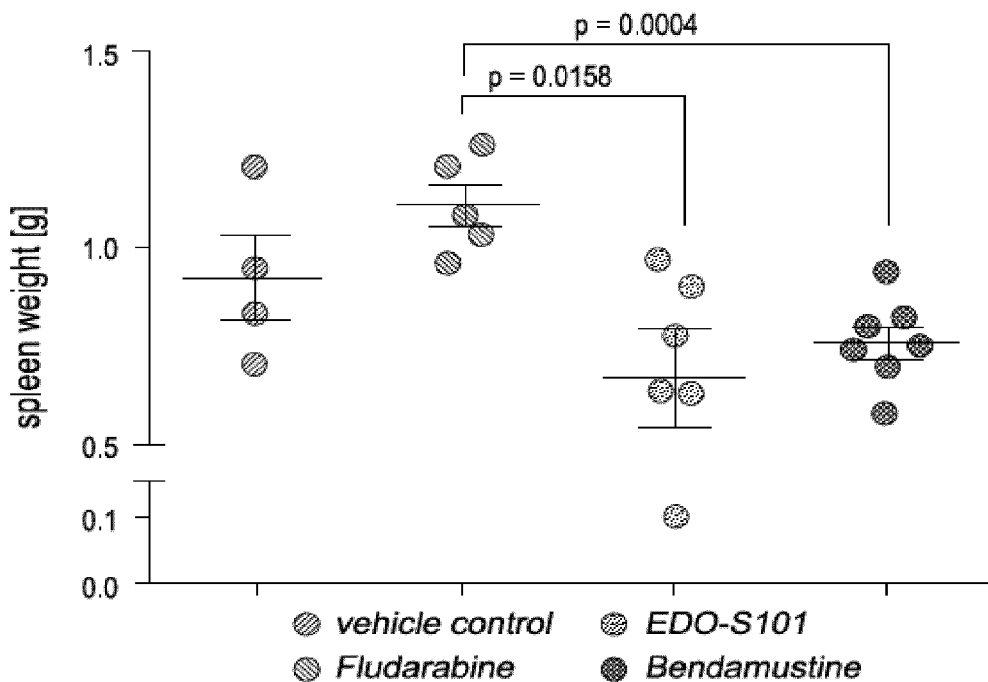

Following sacrifice of the mice on day 22 post-transplantation, the post-mortem spleen weights of each mouse were determined (FIG. 4c). The reduced average spleen weight in mouse cohorts treated with bendamustine or EDO-S101, compared to cohorts treated with fludarabine or a control, corroborate the findings previously discussed in FIG. 4b. Tumour manifestation was therefore shown to be less advanced in cohorts treated with EDO-S101 or single-agent bendamustine, compared to fludarabine treated or control cohorts.

Example 5—In Vivo Analysis of Leukemic Blood Leukocytes (WBC) Count Following Treatment With EDO-S101

Figure 5:
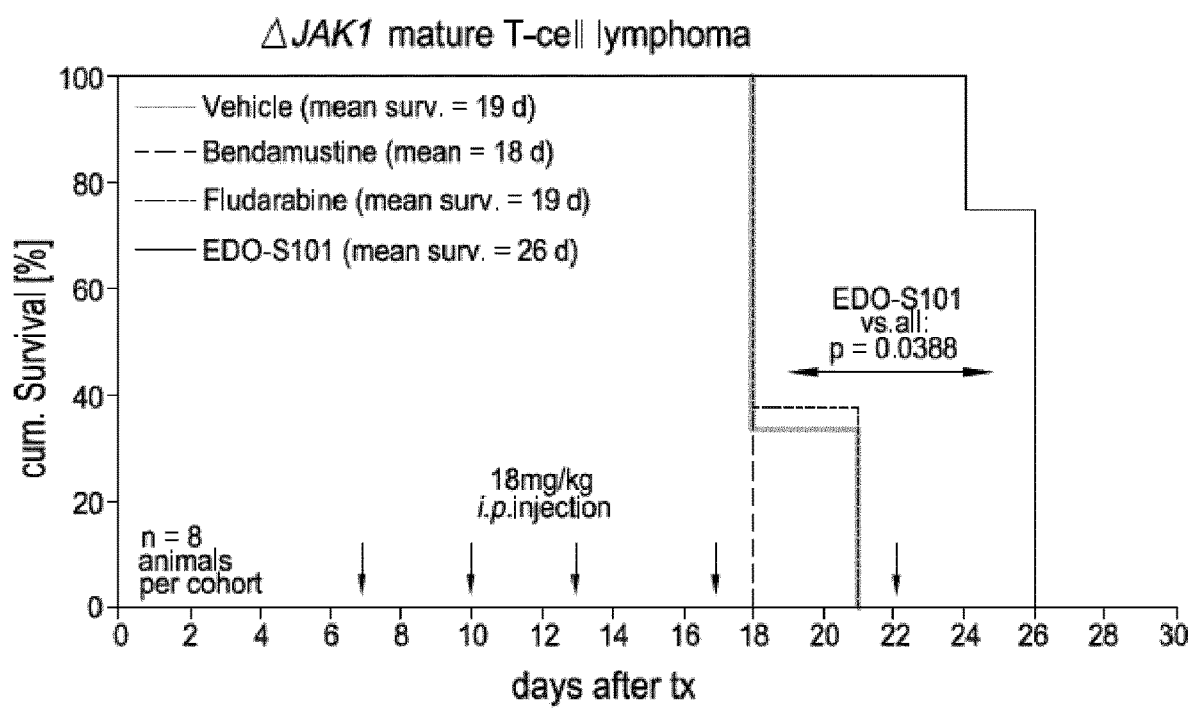
FIG. 5 shows the results of a transfer model for ΔJAK1 mice investigating fludarabine, bendamustine and EDO-S101.

Mice were injected with leukaemia/lymphoma cells derived from ΔJAK1 mice, as previously described (FIG. 5). ΔJAK1 is a model for mature T-cell lymphoma. Mice were divided into four groups at random post-transplantation. Each group was intravenously administered either fludarabine (18 mg/kg), bendamustine (18 mg/kg) or EDO-S101 (18 mg/kg) at the indicated doses on Day 7, Day 10, Day 13, Day 17 and Day 22. The percentage survival of each cohort was plotted as a function of time (FIG. 5). The overall survival (mean survival 26 days) of mice treated with EDO-S101 was found to be significantly prolonged compared to control mice (mean survival 19 days), bendamustine (mean survival 18 days) or fludarabine (mean survival 19 days). These data indicate that treatment with EDO-S101 has a positive effect on the overall survival of mice with T-cell lymphoma, increasing the average survival time by as much as 8 days compared to bendamustine or fludarabine.

The invention claimed is:

1. A kit comprising a therapeutically effective amount of tinostamustine or a pharmaceutically acceptable salt thereof, together with instructions for treating T-cell prolymphocytic leukemia (T-PLL) in a patient in need thereof, wherein said therapeutically effective amount is an amount for administration to the patient at a dosage level effective for treating T-PLL.

2. The kit of claim 1, wherein the therapeutically effective amount is an amount for administration to the patient at a dosage level of from 0.3 mg/m$^2$ to 300 mg/m$^2$ body surface area of the patient.

3. The kit of claim 1, wherein the therapeutically effective amount is an amount for administration to the patient at a dosage level of from 20 mg/m$^2$ to 150 mg/m$^2$ body surface area of the patient.

4. A pharmaceutical composition comprising a therapeutically effective amount of tinostamustine or a pharmaceutically acceptable salt thereof, wherein said therapeutically effective amount is an amount effective for treating T-PLL.

5. The pharmaceutical composition of claim 4, wherein the therapeutically effective amount is an amount for administration to a patient at a dosage level of from 0.3 mg/m$^2$ to 300 mg/m$^2$ body surface area of the patient.

6. The pharmaceutical composition of claim 4, wherein the therapeutically effective amount is an amount for administration to a patient at a dosage level of from 20 mg/m$^2$ to 150 mg/m$^2$ body surface area of the patient.

7. The pharmaceutical composition of claim 4, further comprising a liquid carrier.

8. The pharmaceutical composition of claim 7, wherein the liquid carrier is polyethylene glycol.

9. The pharmaceutical composition of claim 4, wherein the pharmaceutical composition is formulated for intravenous administration.

* * * * *